United States Patent
Carusillo et al.

(10) Patent No.: US 6,958,071 B2
(45) Date of Patent: Oct. 25, 2005

(54) SURGICAL TOOL SYSTEM

(75) Inventors: Steven Carusillo, Kalamazoo, MI (US); Bruce D. Henniges, Kalamazoo, MI (US); Milton Barnes, Fort Worth, TX (US)

(73) Assignee: Stryker Corporation, Kalamazoo, MI (US)

( * ) Notice: Subject to any disclaimer, the term of this patent is extended or adjusted under 35 U.S.C. 154(b) by 406 days.

(21) Appl. No.: 10/251,646

(22) Filed: Sep. 21, 2002

(65) Prior Publication Data

US 2004/0010258 A1 Jan. 15, 2004

Related U.S. Application Data

(60) Provisional application No. 60/395,881, filed on Jul. 13, 2002.

(51) Int. Cl.[7] ........................... A61B 17/32; A61B 17/16
(52) U.S. Cl. ........................... 606/180; 606/170; 606/80
(58) Field of Search ................................. 606/170, 171, 606/234–236, 79–82; 30/340, 277.4, DIG. 5; 408/124; 173/216, 29, 217

(56) References Cited

U.S. PATENT DOCUMENTS

| | | |
|---|---|---|
| 4,071,029 A | 1/1978 | Richmond et al. |
| 4,203,444 A | 5/1980 | Bonnell et al. |
| 4,246,902 A | 1/1981 | Martinez |
| 4,747,820 A | 5/1988 | Hornlein et al. |
| 4,923,441 A | 5/1990 | Shuler |
| 4,951,977 A | 8/1990 | Shutt |
| 5,192,292 A | 3/1993 | Cezana et al. |
| 5,217,479 A | 6/1993 | Shuler |
| 5,269,794 A | 12/1993 | Rexroth |
| 5,376,078 A | 12/1994 | Dinger, III et al. |
| 5,492,527 A | 2/1996 | Glowa et al. |
| 5,669,876 A | 9/1997 | Schechter et al. |
| 5,685,838 A | 11/1997 | Peters et al. |
| 5,792,167 A | 8/1998 | Kablik et al. |
| 5,916,231 A | 6/1999 | Bays |
| 5,993,454 A * | 11/1999 | Longo .......................... 606/80 |
| 6,042,593 A | 3/2000 | Storz et al. |
| 6,152,941 A | 11/2000 | Himes et al. |
| 6,221,088 B1 | 4/2001 | Bays |
| 6,312,441 B1 | 11/2001 | Deng |
| 6,332,891 B1 | 12/2001 | Himes |

FOREIGN PATENT DOCUMENTS

EP 0 729 730 A1 9/1996

OTHER PUBLICATIONS

International Search Report for PCT/US03/12656, mailed Jan. 15, 2004, 6 pages.

* cited by examiner

*Primary Examiner*—Glenn K. Dawson
*Assistant Examiner*—D. Jacob Davis
(74) *Attorney, Agent, or Firm*—Flynn, Thiel, Boutell & Tanis, P.C.

(57) ABSTRACT

A surgical tool system comprising a handpiece and a cutting accessory that is releaseably secured to the handpiece. The handpiece has a gear assembly with two drive heads. The gear assembly turns the drive heads at different rotational speeds relative to each other. The cutting accessory is provided with one of two drive hubs. If the cutting accessory is provided with a first drive hub, the drive hub mates to a first one of the drive heads so as to turn of the speed of that head. If the cutting accessory is provided with a second drive hub, the drive hub mates to the second drive head so as to turn at the speed of that head. Thus, the speed at which the cutting accessory is actuated is a function of the associated drive head.

12 Claims, 23 Drawing Sheets

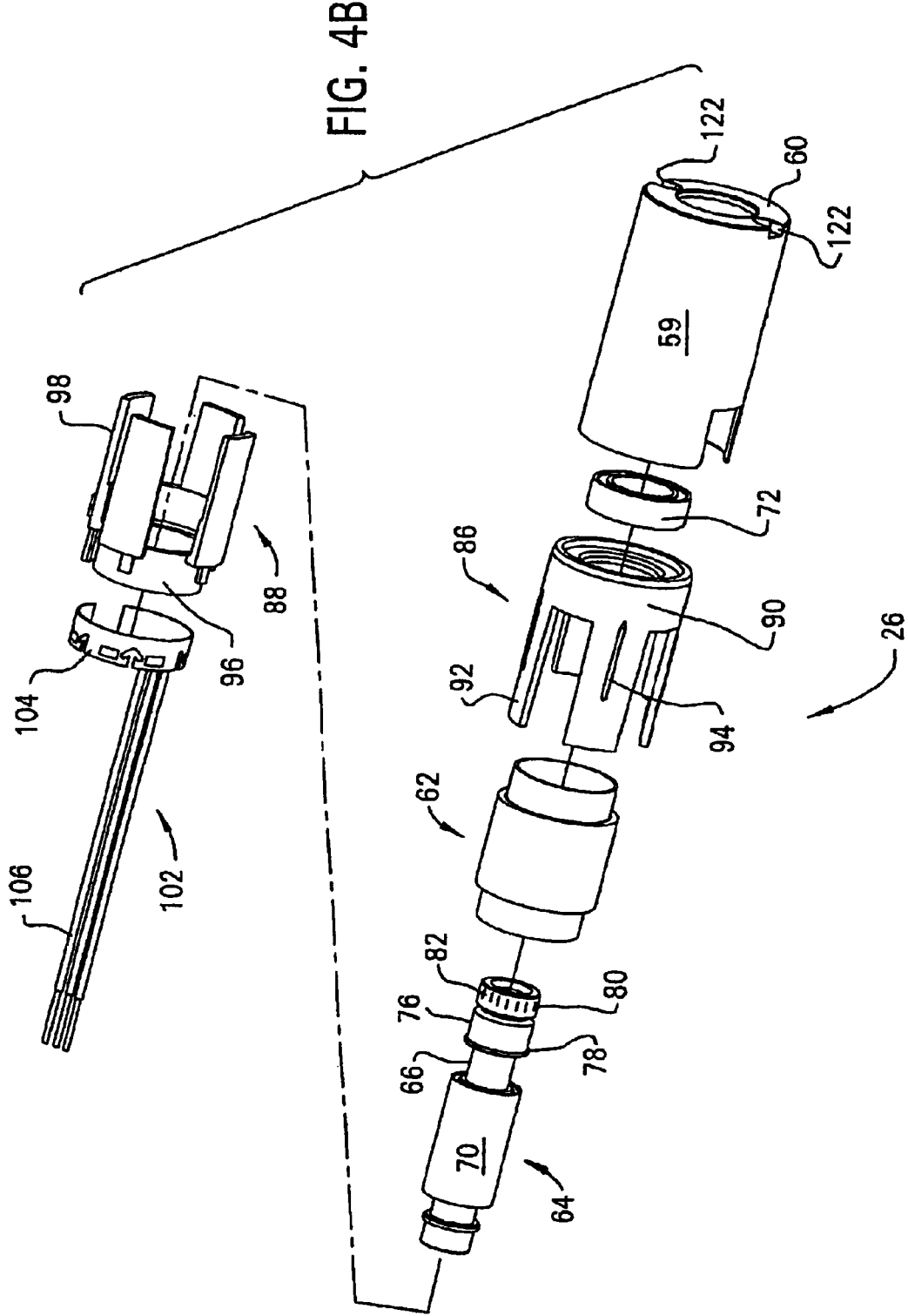

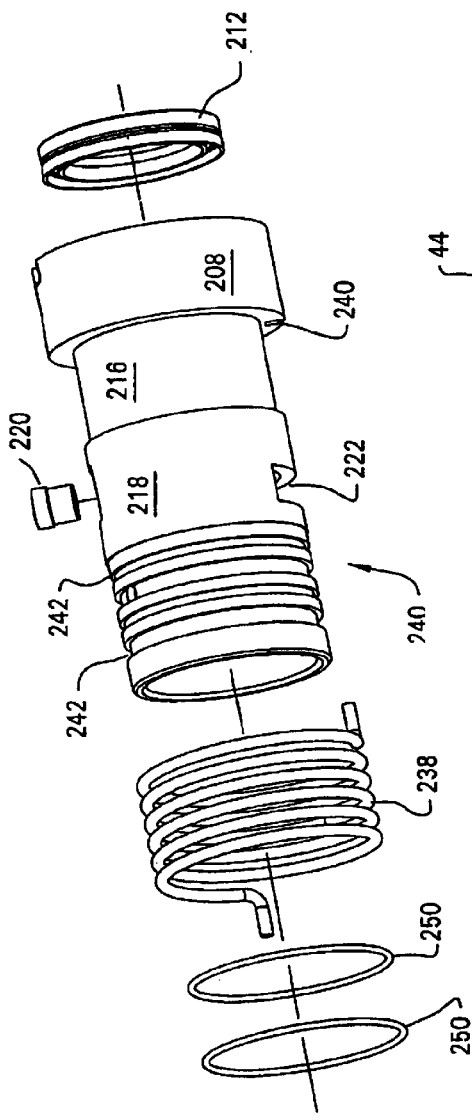
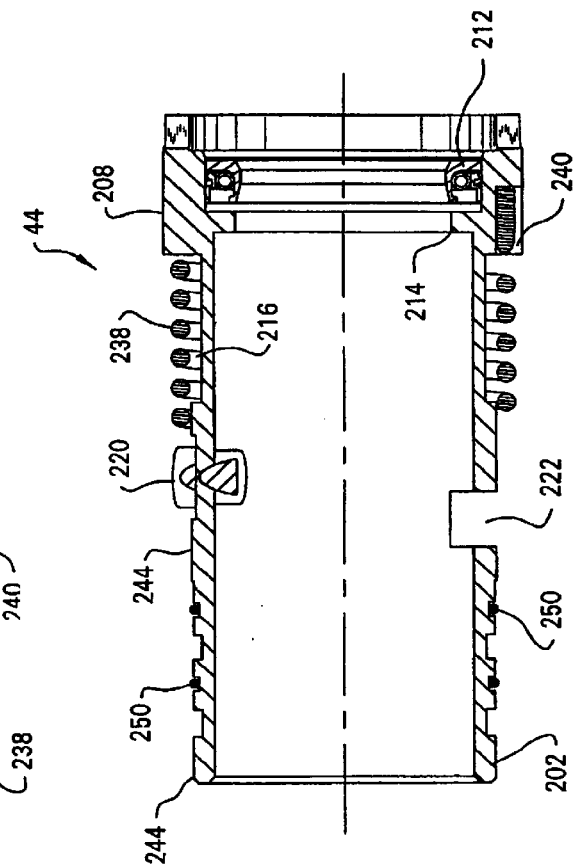
FIG. 8
FIG. 9

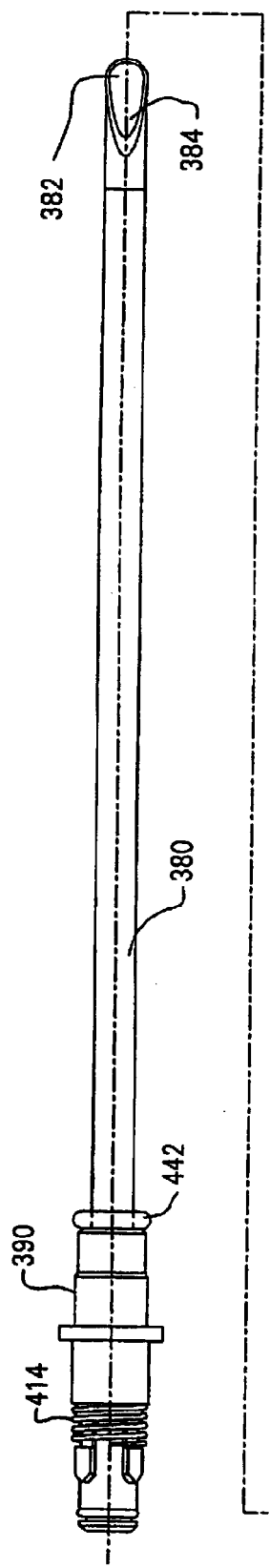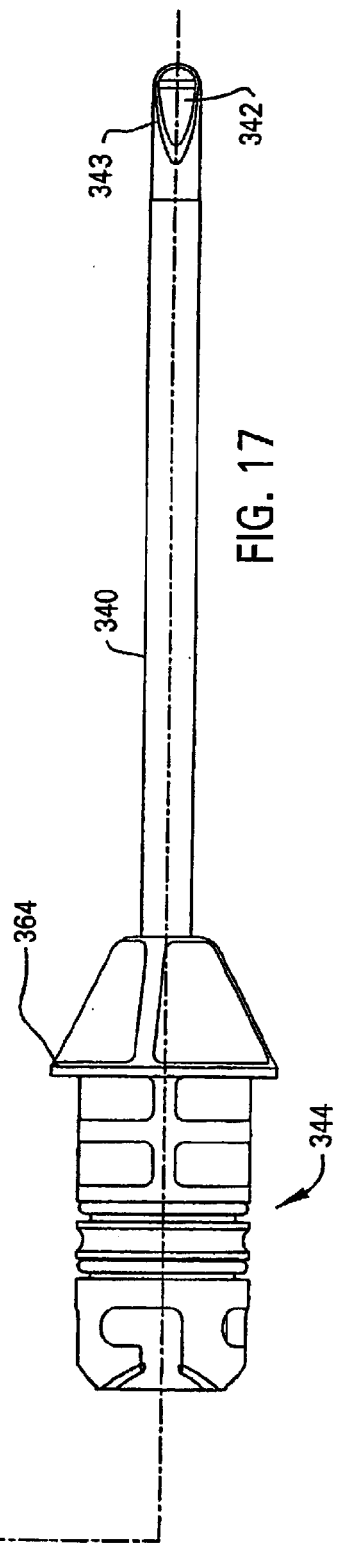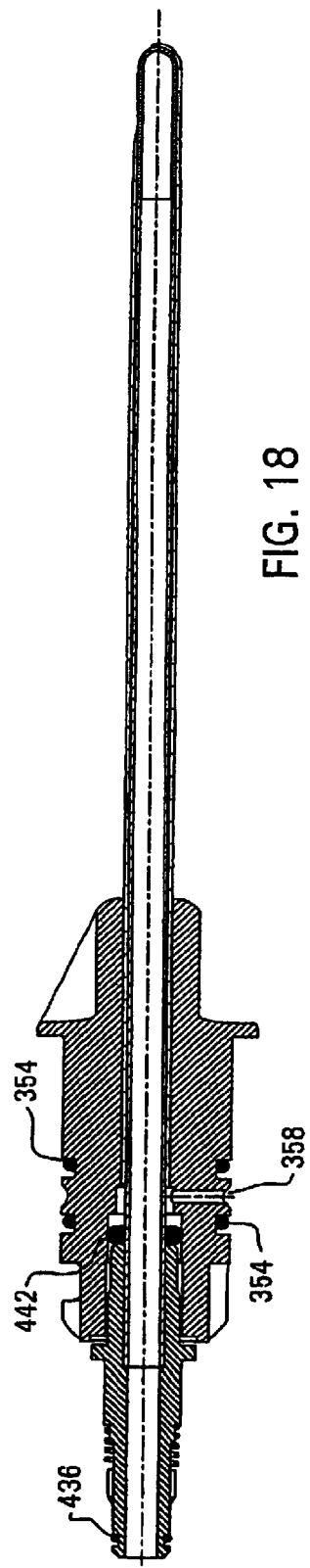
FIG. 17
FIG. 18

# SURGICAL TOOL SYSTEM

RELATIONSHIP TO EARLIER FILED APPLICATION

This application claims priority from U.S. Provisional Patent Application Ser. No. 60/395,881 filed Jul. 13, 2002.

FIELD OF THE INVENTION

This invention relates generally to a surgical tool system. More particularly this invention relates to a surgical tool system with a handpiece capable of driving a cutting accessory attached to the handpiece at a wide range of speeds and that is also capable of supplying irrigating fluid to the cutting accessory automatically, upon attachment of the cutting accessory to the handpiece.

BACKGROUND OF THE INVENTION

The goal of many surgical procedures is to remove, and/or remove so as to shape, body tissue at the site at which the procedure is performed. Surgery on the nasal and sinus cavities and/or the throat frequently involves performing this type of selective removal of tissue. For example, sinus surgery often involves the removal of diseased membranes and/or bone partitions and/or malformed portions of sinus tissue, sometimes referred to as the sinus layer, and bony material entrained in this layer. Orthopedic surgery involves the shaping of bones and soft tissue that form the joints of the skeletal system.

A number of surgical instruments and tools have been developed to facilitate the performance of these surgical procedures. For example, the Applicant's Assignee manufactures a line of surgical tools under the trademark HUMMER that are especially designed to perform nasal, sinus and throat surgery. This line of tools includes a handpiece with an electrically driven motor. Different cutting accessories are designed to selectively be connected to the handpiece. Each cutting accessory typically has a hollow rotating or reciprocating shaft that is housed in a fixed, tube-like, housing. Irrigating solution is flowed to the distal end of the cutting accessory, the end applied to the surgical site, through an annular space between the moving shaft and the complementary housing. This fluid is then drawn away from the surgical site by a suction that is applied through the rotating or reciprocating shaft. This fluid serves as a transport media that flushes debris proximally, away from the patient.

While current surgical tools have proven useful, there are some limitations associated with their use. For example, many surgical handpieces and their complementary attachments are provided with conduits through which suction can be drawn from the complementary attached cutting accessory. Collectively, these handpieces and cutting accessories are constructed so that the coupling of the cutting accessory to the handpiece results in the establishment of a fluid communications path between the suction channel in the cutting accessory and the suction conduit in the handpiece.

However, to date, it has proven difficult to provide a surgical tool system that, upon attachment of the cutting accessory to the handpiece, establishes a fluid path through which irrigating solution is supplied to the cutting accessory. In many commercially available surgical tool systems, in order to establish this fluid path, medical personnel must manually connect a small flexible irrigation fluid supply line associated with the handpiece to an inlet fitting integral with the cutting accessory. Requiring medical personnel to perform this task, and disconnect the line when the accessory is removed from the handpiece, adds to the overall time it takes to remove, replace or change the accessory.

There have been some surgical tool systems proposed that include handpieces with complementary irrigation fluid outlet ports. These systems are designed so that the complementary cutting accessory must be precisely aligned with the handpiece in order to establish the desired fluid communications path. Thus, when a new accessory is fitted to one of these handpieces, care must be taken to properly align these two components. Again, requiring medical personnel to perform this step adds to the overall time it takes to fit the new accessory to the handpiece.

Moreover, in the known surgical tool systems, the need to precisely align the cutting accessory with the handpiece means that the cutting element integral with the cutting accessory must be placed in a select, fixed orientation relative to the handpiece. Thus, in these systems, the surgeon is not able to position the cutting accessory so that, relative to the handpiece, the cutting element is in an orientation that makes it more convenient, or even possible, for the surgeon to perform some surgical tasks.

Moreover, like any motor, the motors integral with handpieces of surgical tool systems only operate within a given operating range. The motors integral with some handpieces operate within a relatively limited rotational speed range. This is especially true for handpieces that include brushless, sensorless motors. These motors, owing to the fact that the back EMF signals they produce are employed to control their operation, have operational rotational speed ranges that are less than similar motors in which sensors are installed that provide an indication of rotor position.

The limited rotational speed range of some handpiece motors means that the accessories attached to these headpieces can only be driven through a relatively limited range of speeds. This means that sometimes a cutting accessory, such as a laryngeal cutter cannot be driven at a relatively low speed that might be useful. Similarly, another accessory, such as a bur cannot be driven at a relatively high speed that may be sometimes desired for its operation.

One solution to this problem is to provide the surgeon with two different handpieces; one with a relatively slow speed motor, the second with a relatively high speed motor. A second solution to this problem has been to provide intermediate attachments between the handpiece and the cutting accessory. Typically, this attachment is connected to a handpiece with a relatively high speed motor. Internal to the attachment is a gear assembly that reduces the output speed at which the associated accessory is driven. A disadvantage of both of these solutions is they require the introduction of an extra component, either the supplemental handpiece or the ancillary attachment to the operating room. Moreover, the medical personnel using the components of these systems must spend time ensuring that the cutting accessory is attached to the appropriate handpiece or intermediate attachment in order to operate the accessory at the desired speed. The time making sure this connection is established adds to the overall time it takes to make the cutting accessory available to perform the desired surgical procedure.

SUMMARY OF THE INVENTION

This invention is related to a new and useful surgical tool system. The system of this invention includes a handpiece to which complementary cutting accessories are removably attached. The handpiece has a motor for driving the cutting accessories. A gear train is attached to the motor. The gear train has plural rotating output heads, each of which rotates at a different speed. Each cutting accessory is provided with a drive hub that is dimensioned to be coupled to one of the specific output shafts. Thus, the coupling of the accessory drive hub to the complementary specific output shaft results in the cutting accessory being rotated at the appropriate speed for its operation.

Internal to the handpiece of this invention there is a conduit through which irrigating fluid is supplied. This conduit opens into a discharge port. The cutting accessories of this system are provided with a complementary circumferential conduit for receiving the irrigating fluid.

BRIEF DESCRIPTION OF THE DRAWINGS

The invention is pointed out with particularity in the claims. The above and further features and benefits of the invention may be better understood by reference to the following description in combination with the accompanying drawings, in which:

FIGS. 4A and 4B are, respectively, exploded and cross-sectional views of the motor of the handpiece;

FIG. 8 is an exploded view of the lock assembly;

FIG. 9 is a cross-sectional view of the lock assembly;

FIG. 17 is a partially exploded view of one cutting accessory of this invention;

FIG. 18 is a cross-sectional view of the cutting accessory of FIG. 17;

DETAILED DESCRIPTION

Figure 1:
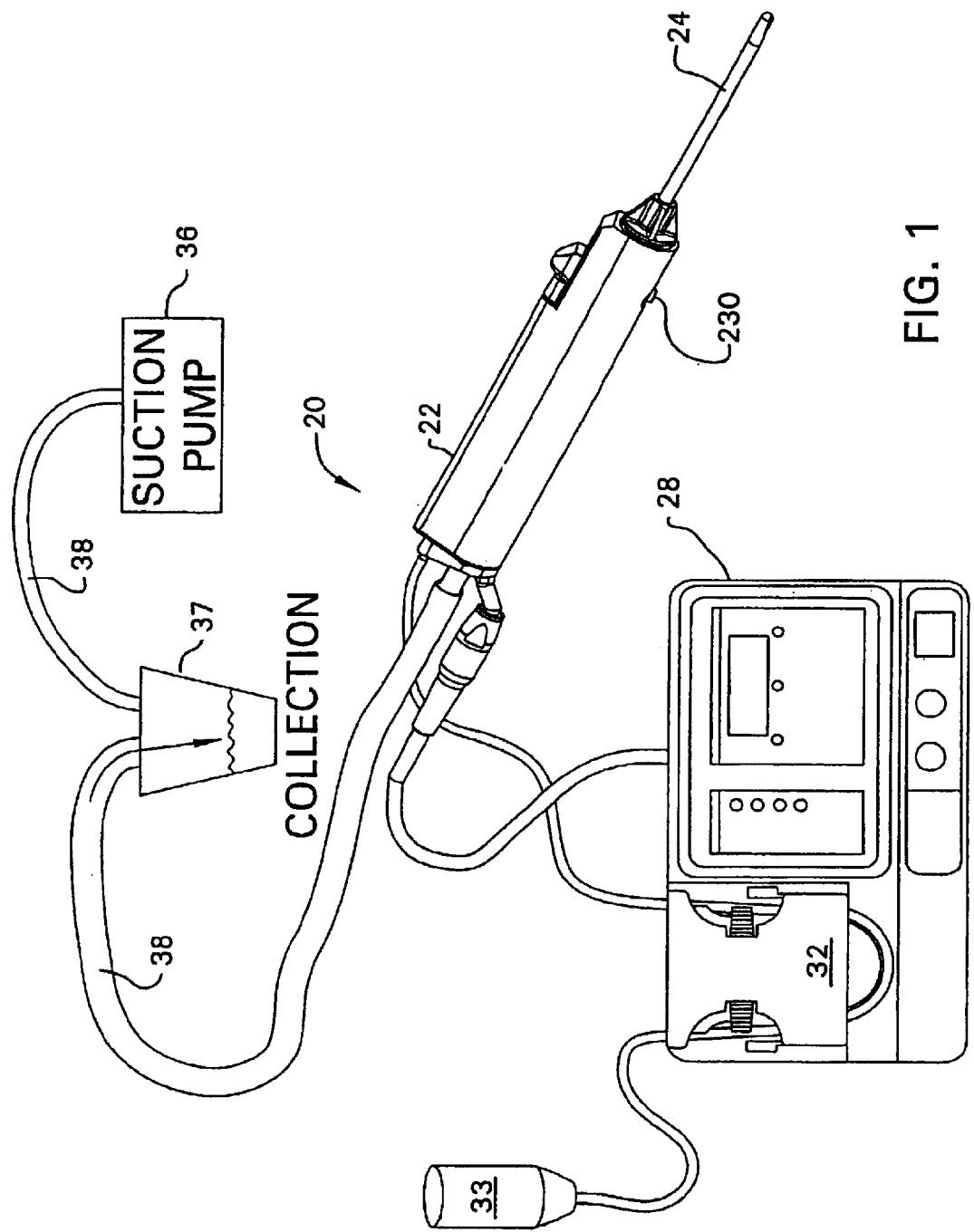
FIG. 1 is an overall view of the components of the surgical system of this invention.
Figure 2:
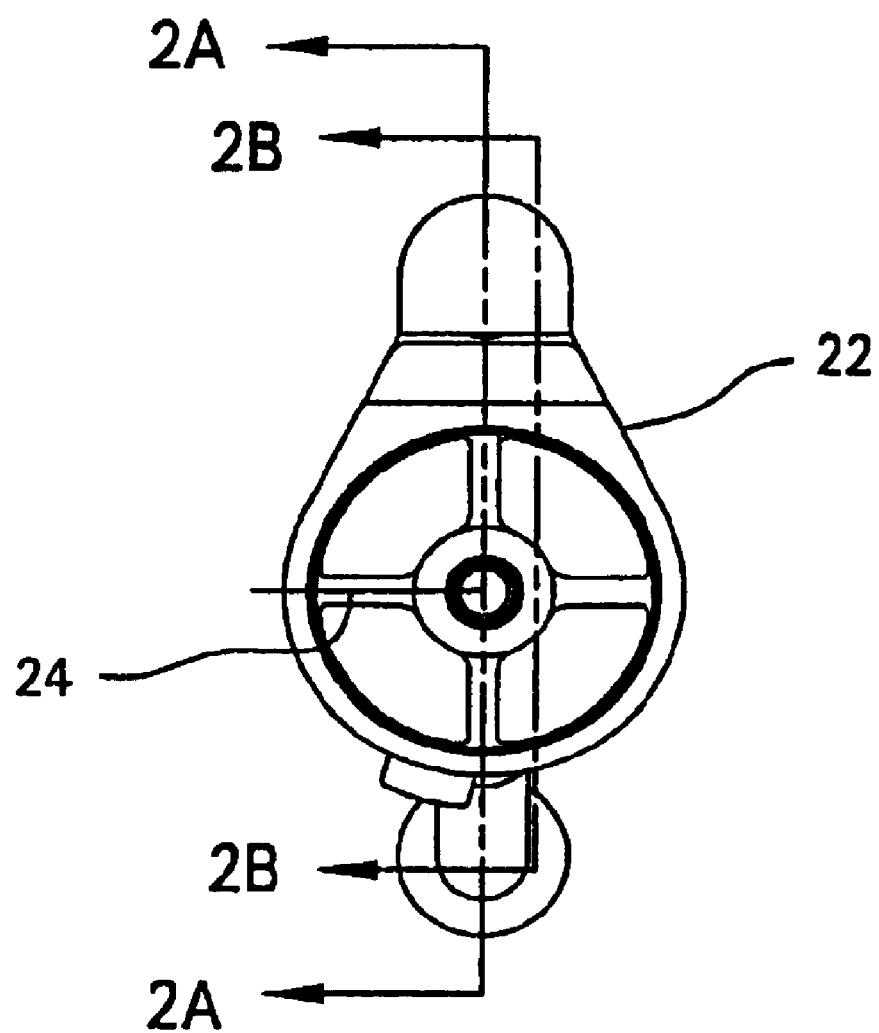
FIG. 2 is a view of the front of the handpiece of the surgical tool system of this invention.
Figure 2A:
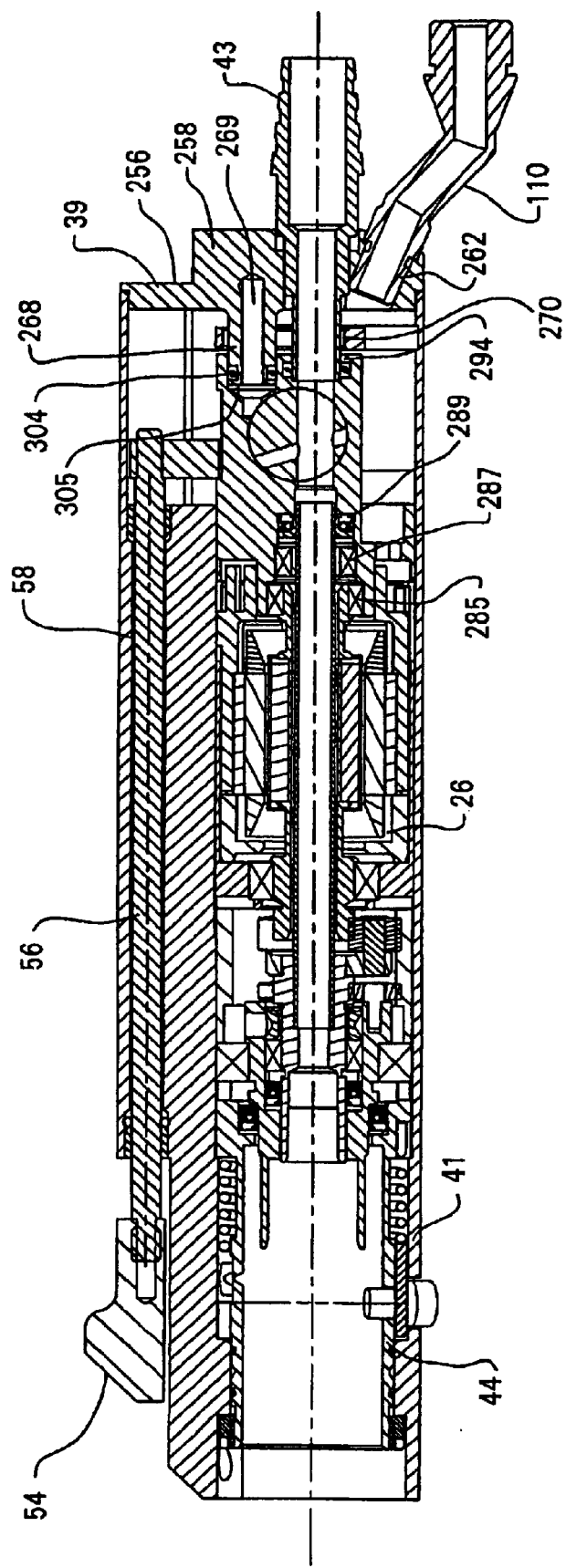
FIG. 2A is a cross-sectional view of the handpiece taken along line 2A—2A of FIG. 2.

FIGS. 1, 2 and 2A illustrate a surgical tool system 20 of this invention. System 20 includes a handpiece 22 to which a cutting accessory 24 is removably attached. Internal to the handpiece 22 is a motor 26 that actuates tile cutting accessory 24. Power to actuate the motor 26 is supplied from an external control console 28. One such control console and some of its internal circuitry are disclosed in the Applicant's Assignee's U.S. Pat. No. 5,689,159, SURGICAL TOOL SYSTEM WITH BRUSHLESS, SENSORLESS MOTOR, issued 18 Nov. 1997 and U.S. Pat. No. 6,017,354, INTEGRATED SYSTEM FOR POWERED SURGICAL TOOLS, issued 25 Jan. 2000, both of which are incorporated herein by reference. Handpiece 22 is connected to control console 28 by a power cable 30 that extends from the proximal end of the handpiece. (In this application, "proximal" is understood to be towards the surgeon holding the handpiece 22; "distal" is understood as being away from the surgeon.)

A pump 32 is attached to control console 28. Pump 32 supplies irrigating fluid from a container 33 to the handpiece through supply line 34. As described hereinafter, this irrigating fluid is flowed through the handpiece to the cutting accessory 24. The handpiece 22 is connected to a suction pump 36 through a suction line 38. The distal end of the cutting accessory 22 is provided with windows 342 and 382 (FIG. 17). When the suction pump 36 is actuated, a suction is drawn through accessory windows 342 and 382, the cutting accessory 24 and through the handpiece 22 to a collection receptacle 37. Collection receptacle 37 is located between two sections of suction line 38. The material drawn through the system 20 by pump 36 is discharged into the collection receptacle 37. This sub-assembly thus allows irrigating fluid and debris present at the surgical site to be drawn away from the site through the surgical tool system 20.

Handpiece 22, now described by reference to FIGS. 2, 2A, 2B and 3, includes an elongated body 40 to which the other components of the handpiece are housed and/or to which these components are attached. The body 40 is formed with a longitudinally extending main bore 41 in which most of the components internal to the handpiece 22 are located. A back cap 39 covers the proximal end of body 40 including bore 41. The distal end, the front end, of bore 41 is open to receive the proximal end of cutting accessory 24.

Motor 26 is one component disposed in bore bore 41. A gear train 42 is located in bore 41 forward of motor 26. Gear train 42 includes a set of gears and two output heads. The gears reduce, step-down, the speed of the rotational moment produced by the output shaft of the motor. More specifically, the gear train rotates each output head at a specific ratio relative to the output speed of the motor shaft. The attached cutting accessory 24 is provided with one of two drive hubs. Each drive hub is dimensioned to engage a specific one of the output shafts of the gear train 42. Thus, the speed at which the handpiece drives the cutting accessory 24 is a function of which output head is engaged by the accessory.

Motor 26 and gear train 42 are both cannulated. Thus, collectively these assemblies are provided with components that define a conduit that extends axially through the handpiece 22. This conduit is connected to suction line 38 through a fitting 43 attached to the rear, proximal end, of the handpiece 22. This conduit serves as the conduit through which a suction is drawn through the cutting accessory 24 and handpiece 22.

A lock assembly 44 is disposed in body bore 41 forward of the gear train 42. The lock assembly 44 releasably holds the proximal end of the cutting accessory 24 in bore 41.

Figure 2B:
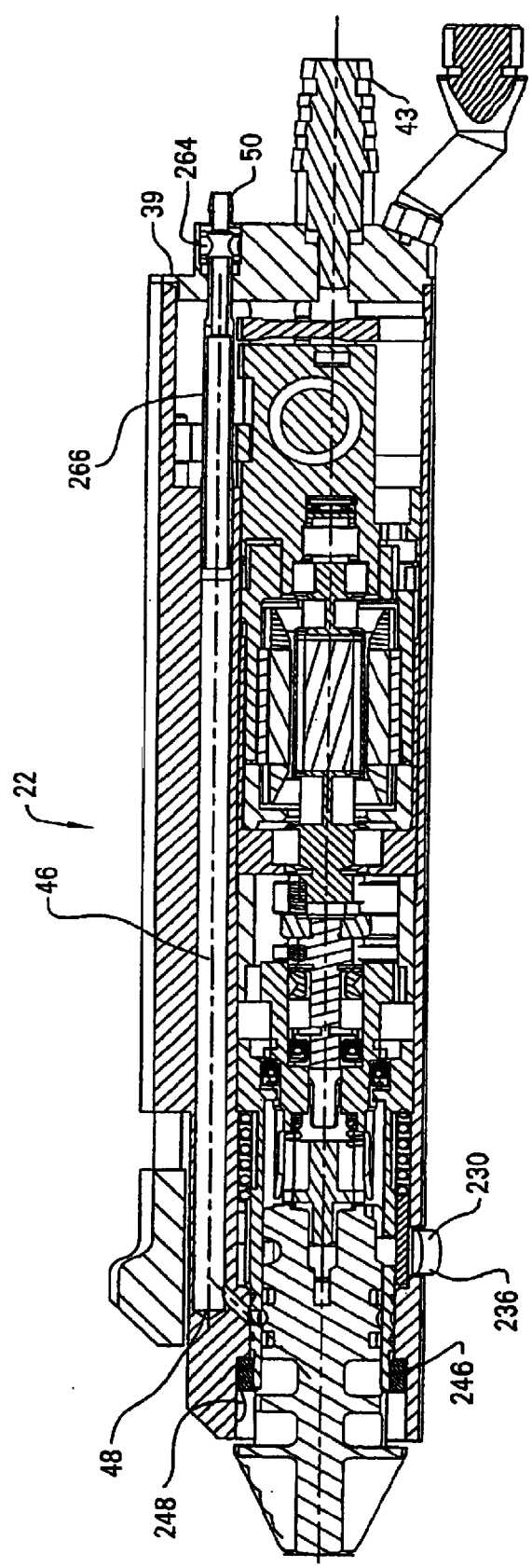
FIG. 2B is a cross-sectional view of the handpiece taken along line 2B—2B of FIG. 2.

The handpiece body 40, as best seen in FIGS. 2A and 2B, is formed with a longitudinally extending fluid supply bore 46 that is located above main bore 41. The body 40 is further formed so that fluid supply bore 46 is offset from the plane that extends along the lateral axis of the body. Fluid supply bore 46 extends from the proximal end of body 40 towards the distal end. The fluid supply bore 46 does not extend completely through body 40. Instead, the fluid supply bore 46 terminates before the distal end of the handpiece 22. A small discharge bore 48 extends diagonally forward from the distal end of the fluid supply bore 46 into main bore 41. An inlet fitting 50 that extends from end cap 39 serves as the member that establishes a fluid communication path from the external supply line 34 to the fluid supply bore 46.

A valve 52 is rotatably mounted in body bore 41 immediately rearward of the motor 26. Valve 52 is selectively positioned to regulate fluid flow through the conduit that extends through the motor 26 and gear train 42. Depending on the position of valve 52, this conduit is either: connected to the suction fitting 43; or connected to the inlet fitting 50. The setting of valve 52 is controlled by button 54 that is slidably mounted to the distal front end of the handpiece body 22. A linkage rod 56 connects button 54 to the valve 52. Rod 56 is disposed in a bore 58 formed in the handpiece body 40 that extends parallel to and is located above main bore 41.

Figure 4A:
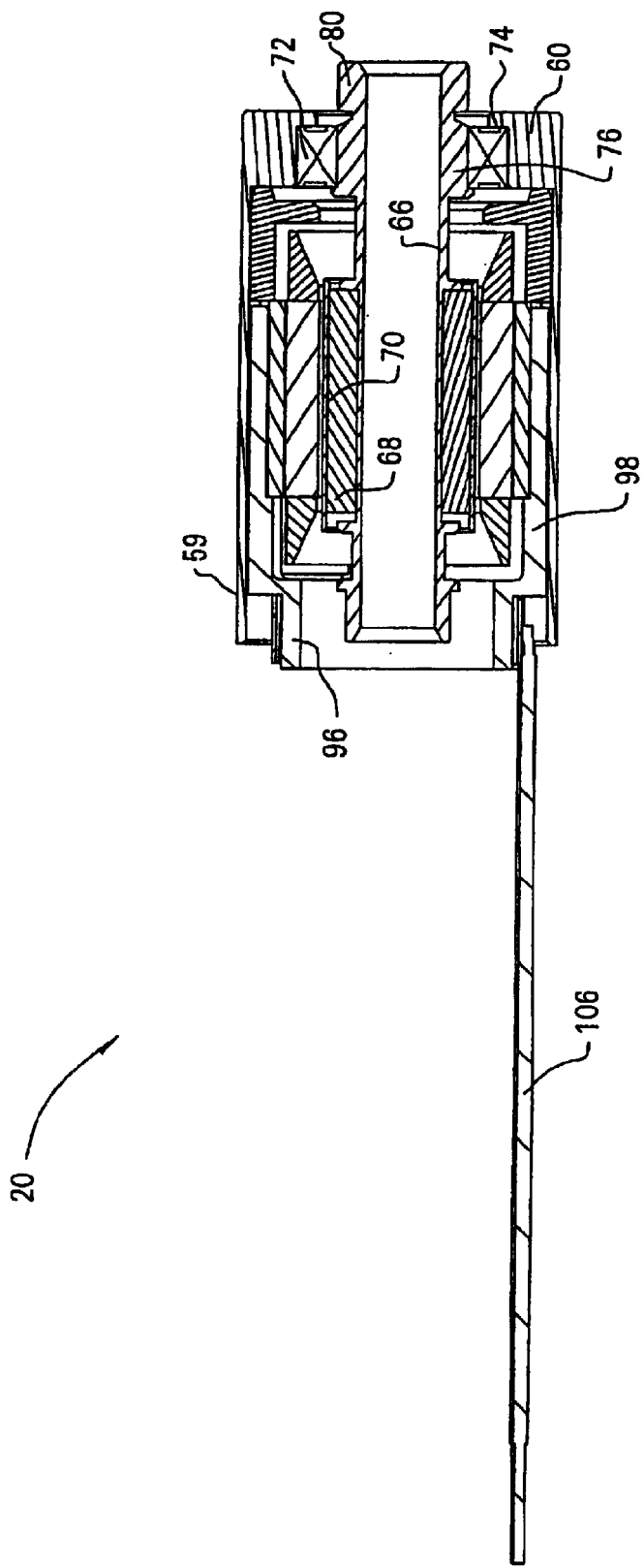

Motor 26, which is a brushless, sensorless motor, is now described in detail by reference to FIGS. 4A and 4B. The motor 26 includes a generally tubular-shaped, open at both ends housing 59 that is closely fitted in bore 41. Housing 59 is further formed so as to have an inwardly directed lip 60 that extends circumferentially around the front end of the housing. A field coil assembly 62 and rotor assembly 64 are disposed in housing 59 to, respectively, form the primary static and rotating parts of the motor 26. The field coil assembly 62, which is generally tubular in shape, includes the static windings of the motor 26, (windings not identified). Rotor assembly 64 is disposed inside the field coil assembly 62. The rotor assembly includes a tubular shaft 66. A plurality of magnets 68 are disposed around the portion of shaft 66 that is subtended by the windings of the field coil assembly 62. Magnets 68 are encased in a cylindrical sleeve 70.

Shaft 66 of the rotor assembly 64 is dimensioned to extend forward of motor housing 59. A bearing assembly 72 rotatably holds shaft 66 to housing 59. Specifically, the bearing assembly 72 is press fit in a groove 74 that has a rectangular cross-sectional profile that extends circumferentially around the inner parameter of housing lip 60.

The bearing assembly 72 has an inner race, (not illustrated) against which a shoulder 76 of shaft 66 is fitted. Shoulder 76, it will be observed, has an outer diameter greater than that of the main body of shaft 66. The shaft 66 is further formed so that a small ridge 78 extends outwardly from the proximal end of the shoulder and extends circumferentially around the shoulder. Ridge 78 prevents the forward movement of shaft 66.

Rotor shaft 66 is further formed to have a head 80 located forward of shoulder 76 that is located in front of housing 59. The outer surface of head 80 is formed to have teeth 82. Teeth 82 engage complementary gears of the gear train 42.

Field coil assembly 61 and rotor 64 are encased in front and back shells 86 and 88, respectively, formed of non-conductive material such as liquid crystal polymer. Front shell 86 has a ring-shaped head 90. Extending rearwardly from head 90 are a number of spaced apart, parallel, rearwardly extending fingers 92. Small raised ribs 94 extend outwardly from the outer surfaces of fingers 92. When the front shell is fitted within housing 59, ribs 94 ensure a tight fit of the shell. Back shell 88 has a ring shaped base 96. Parallel, spaced apart fingers 98 extend forward from base 88. When motor 26 is assembled, fingers 98 of the back shell 88 seat in the interstitial spaces between fingers 92 of front shell 86. Shells 86 and 88 thus provide a barrier between the field coil and rotor assemblies 64 and 66, respectively, and the motor housing 59.

A flex circuit 102 that is wrapped into a C-shape is disposed around the outer surface of back shell base 88. Not shown are the conductive traces formed on the flex circuit 102. These traces form the conductive links to the windings integral with the field coil assembly 62.

A set of insulated conductors 106 extends rearwardly from flex circuit 102 through body bore 41. Conductors 106 are connected to a second set of conductors, conductors 108, now described by reference to FIGS. 2A and 3, that extends rearwardly out of the handpiece body 40. Specifically, conductors 108 extend through an angled tube 110 that extends rearwardly from back cap 39. A plug 112 extends from tube 110. Conductors 108 extend through plug 112 and power cable 30. Plug 112 is the distal end plug of power cable 30 and conductors 108 are the power conductors internal to the cable.

Figure 5A:
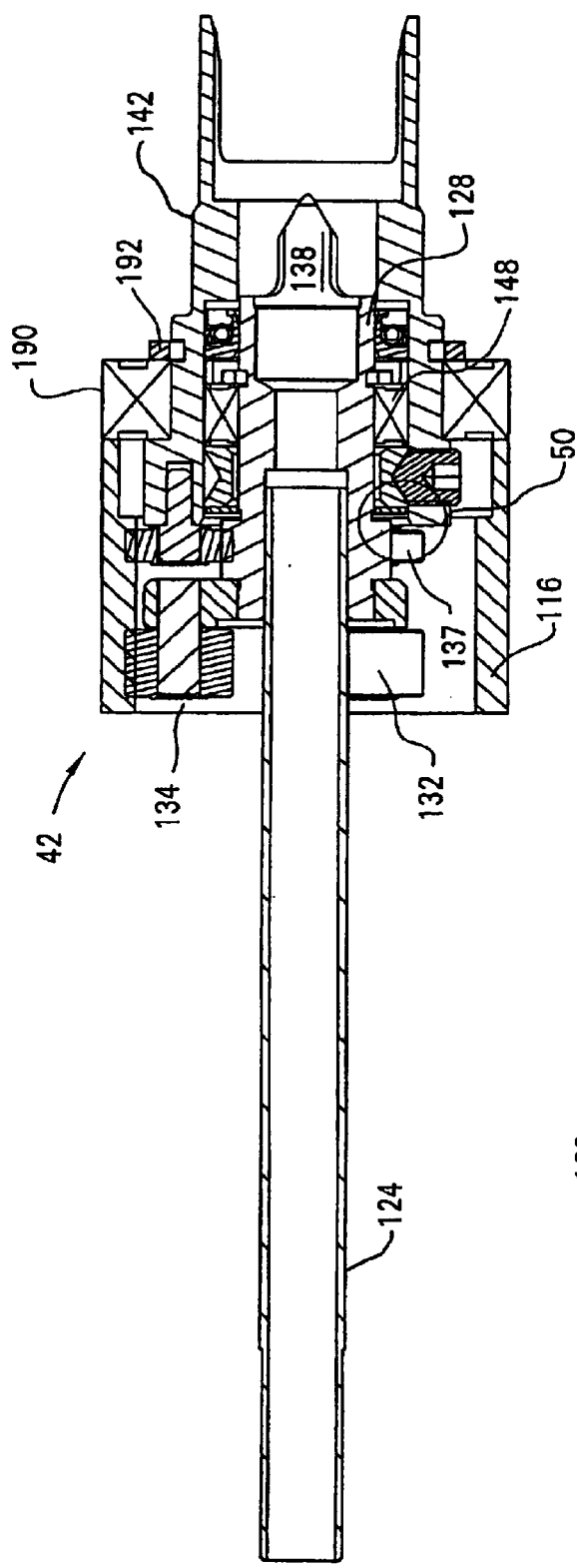
FIGS. 5A and 5B are, respectively, cross-sectional and exploded views of the gear train assembly of the handpiece.
Figure 5C:
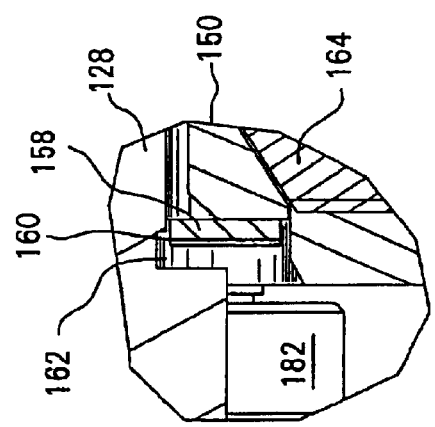
FIG. 5C is a detailed cross-sectional view of the interface around the proximal end of the bearing ring of the gear train assembly.

The gear train 42, is now described by reference to FIGS. 5A, 5B and 5C. The gear train 42 includes a cylindrical housing 116 in which the other components of the gear train are housed. Housing 116 is designed be closely slip-fitted in handpiece bore 41. The inner surface of housing 116 is formed with teeth 118 so that the housing functions as the outer static ring of two planetary gear assemblies that comprise the gear train. Housing 116 is also formed with two rearwardly extending tabs 120, (one tab shown). Tabs 120 seat in complementary slots 122 formed in motor assembly housing 59 (FIG. 4B). Tabs 120 prevent gear train housing 116 from rotating relative to the motor 26.

Gear train 42 also includes a motor tube 124 that is disposed in the gear train housing 116 and extends rearwardly beyond the proximal end of the rotor shaft 66. The distal end of the motor tube 124, the end disposed in the gear train housing 116, is seated in the center bore of a high speed head 128. High speed head 128 is shaped to have a through bore. The distal end of the motor tube 124 is press fit in a rearward facing counterbore that extends coaxially with the through bore. (High speed head bores not identified). Thus, the motor tube 124 and high speed head 128 rotate in unison. A triangularly-shaped planet carrier 130 is press fit over the proximal end of the high speed head 128 so that the head and carrier rotate in unison. Three planet gears 132 are rotatably mounted to pins 134 that extend rearwardly from carrier 130. When the handpiece 22 of this invention is assembled, planet gears 132 engage both the teeth 82 of motor rotor shaft 66 and the inner teeth 118 of gear train housing 116.

Immediately forward of planet carrier 130, high speed head 128 is formed to have a toothed ring 137. The distal end of high speed head 128 is formed to have two diametrically opposed, forward-directed, pointed teeth 138. When a cutting accessory with a high speed drive hub is coupled to the handpiece 22, teeth 138 engage the drive hub.

Figure 6A:
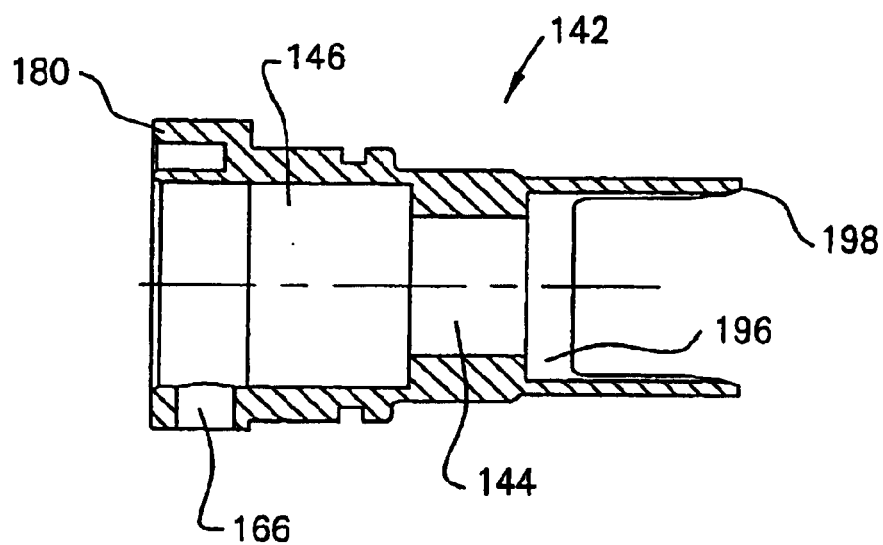
FIGS. 6A and 6B are, respectively, cross-sectional and perspective views of the low speed head of the gear train assembly.
Figure 6B:
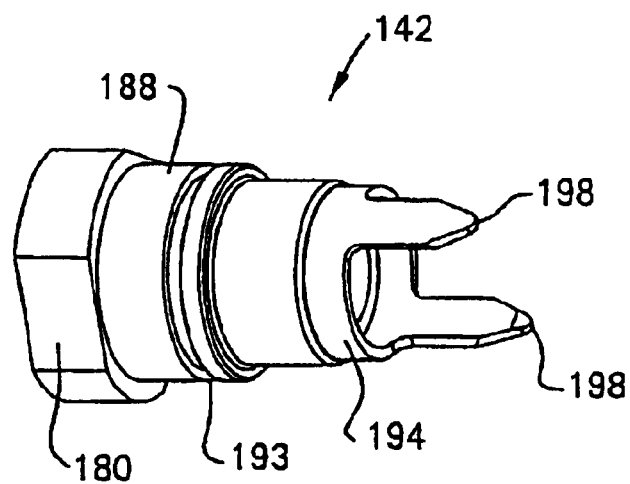

A low speed head 142 is rotatably fitted over the portion of the high speed head 128 located forward of planet carrier 130. The low speed head 142, seen best in FIGS. 6A and 6B, is formed to have a through bore 144. The section of high speed head 128 distal to toothed ring 137 and proximal to pointed teeth 138 are seated within a rearwardly directed counterbore 146 coaxial with bore 144. Collectively, the high and low speed heads 128 and 142, respectively, are shaped so that teeth 138 are spaced inwardly from the inner wall of low speed head 128 that defines bore 144. The high and low speed heads 128 and 142, respectively, are further shaped so that there is an annular gap between the outer surface of the high speed head 128 and the inner surface of low speed head 142 that defines counterbore 146.

A bearing assembly 148 located in counterbore 146 rotatably holds the high speed head 128 in low speed head 142. A bearing ring 150 is located against the proximal-facing end of bearing assembly 148. Bearing ring 150, as seen best in FIGS. 5B and 6C, is formed to have a flat inner surface 152. The bearing ring is formed so that the diameter of inner surface 152 is slightly larger than the outer diameter of the adjacent underlying section of the high speed head 128. Bearing ring 150 is further formed so that there is a V-shaped, circumferentially extending groove 156 in the outer surface of the ring.

Two washers 158 and 160 are located adjacent the proximal facing end of bearing ring 150. Washer 160 prevents bearing ring 150 from pressing down against the toothed ring 137. Washer 158 is located between the bearing ring 150 and washer 158. Washer 158 provides a low-friction interface between bearing ring 150 and washer 160. Seen in FIG. 5C is an undercut 162 provided forward of toothed ring 137 in low speed head 142 for manufacturing reasons.

A set screw 164 longitudinally holds the low speed head 142 to bearing ring 150. Specifically, set screw 164 is seated in a threaded bore 166 that extends radially through the low speed head 142. Set screw 164 has a conical tip, (not identified) that seats in the groove 156 of bearing ring 150. Set screw 164 thus captures the high speed head 128 in the low speed head 142.

A retaining ring 167, located forward of bearing assembly 148, blocks rearward movement of the high speed head 128. The retaining ring, which is C-shaped, is snap-fitted in a circumferential groove 168 formed in the high speed head 128 located immediately forward of the portion of head 128 subtended by bearing assembly 148.

A dynamic seal 170 is located in the base of counterbore 146 of low speed head 142. Seal 170 extends between the inner surface of the low speed head 142 that defines counterbore 146 and the outer surface of the high speed head 128 from which teeth 138 extend forward. Seal 170, includes a U-shaped ring of flexible, low friction material and a metallic circular spring formed in the center of the ring that presses the sides outwardly, (seal components not identified). Dynamic seal 170 thus forms a liquid-tight barrier between the high and low speed heads 128 and 142, respectively.

A ring-shaped spacer 176 surrounds and is spaced from retaining ring 167. The opposed proximal and distal ends of spacer 176 abut, respectively, the outer race of bearing assembly 148 and the ring of dynamic seal 170. Spacer 176 thus prevents the dynamic seal 170 from bearing against retaining ring 167.

The distal sections of low speed head 142 generally have a circular cross-sectional profile. However, low speed head 142 is further formed to have a proximally-located base 180 that has a triangular profile and is further shaped to extend outwardly beyond the other sections of the head 142. Base 180 is the portion of the low speed head 142 in which threaded bore 166 is formed. Three planet gears 182 are mounted to pins 184 that extend rearwardly from positions near the apices of base 180. When handpiece 22 is assembled, gears 182 engage both the toothed ring 137 of the high speed head and the toothed inner surface of gear train housing 116.

Figure 5B:
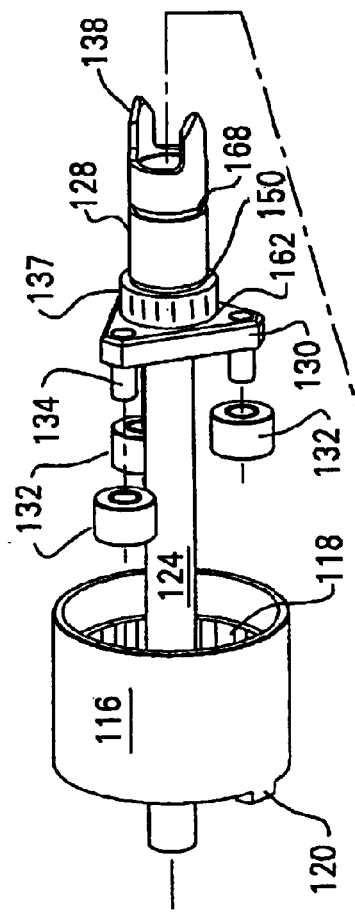
Figure 5B:
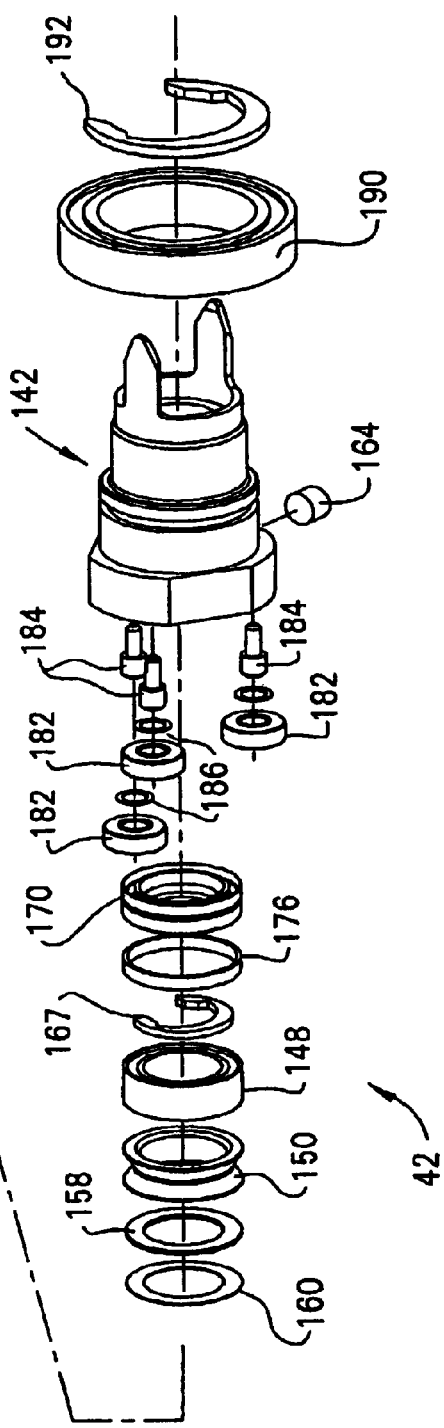
Figure 6C:
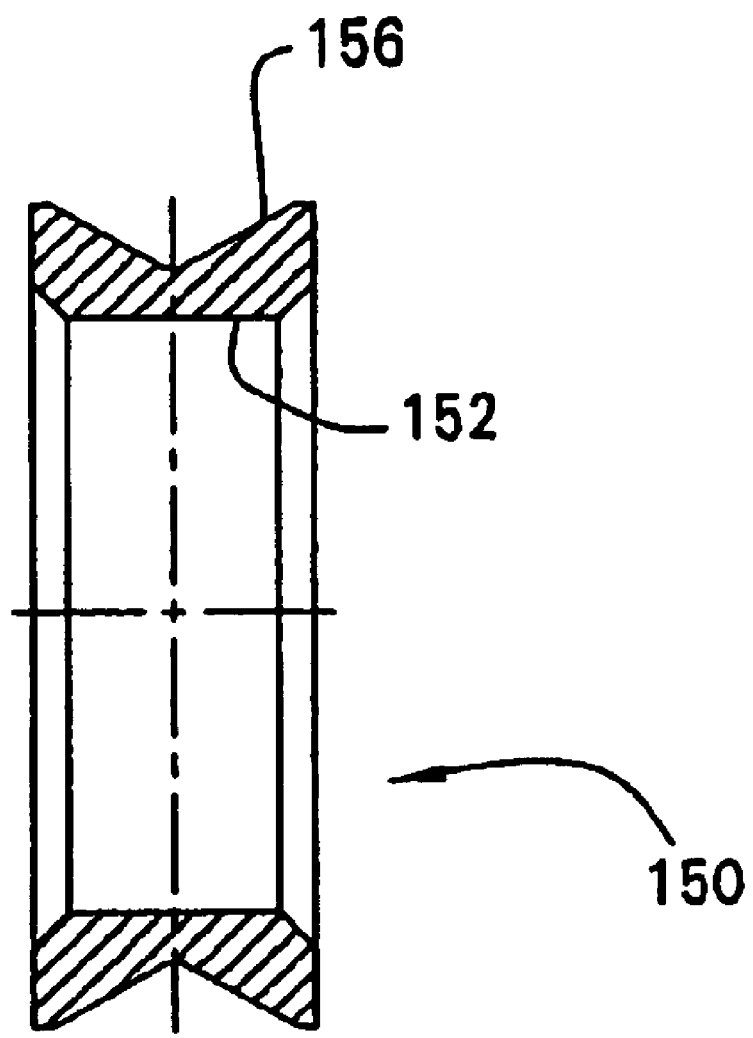
FIG. 6C is a cross-sectional view of the bearing ring of the gear train assembly.

As seen in FIG. 5B, washers 186 are located around pins 184 between gears 182 and the adjacent proximal facing surface of base 180 of the low speed head 142. Washers 186 reduce the friction of the gears-to-head contact.

Immediately distal to base 180, low speed head 142 is formed with a shoulder section 188 that has a circular profile. A bearing assembly 190 extends between shoulder section 188 and the adjacent inner wall of the handpiece body 40 that defines the main bore 41. Bearing assembly 190 thus rotatably centers the low speed head 142 in bore 41. When the handpiece 22 is assembled the outer race of bearing assembly 190, (race not illustrated) seats against the adjacent distally-directed end face of housing 116. A C-shaped retaining ring 192 is located around the distally-directed face of the inner race of bearing assembly 190, (race not illustrated). Retaining ring 192 is snap-fitted in a circumferential groove 193 formed in the head shoulder section 188.

Located forward of the portion of low speed head 142 that defines bore 144, the head 142 is formed to have a nose section 194 of reduced diameter than the adjacent proximal section. Nose section 194 forms a second counterbore 196 also coaxial with bore 144. Two diametrically opposed, spaced apart pointed teeth 198 extend forward from nose section 194. When a cutting accessory 24 with a low speed drive hub is coupled to the handpiece 22, teeth 198 engage the hub.

Figure 7:
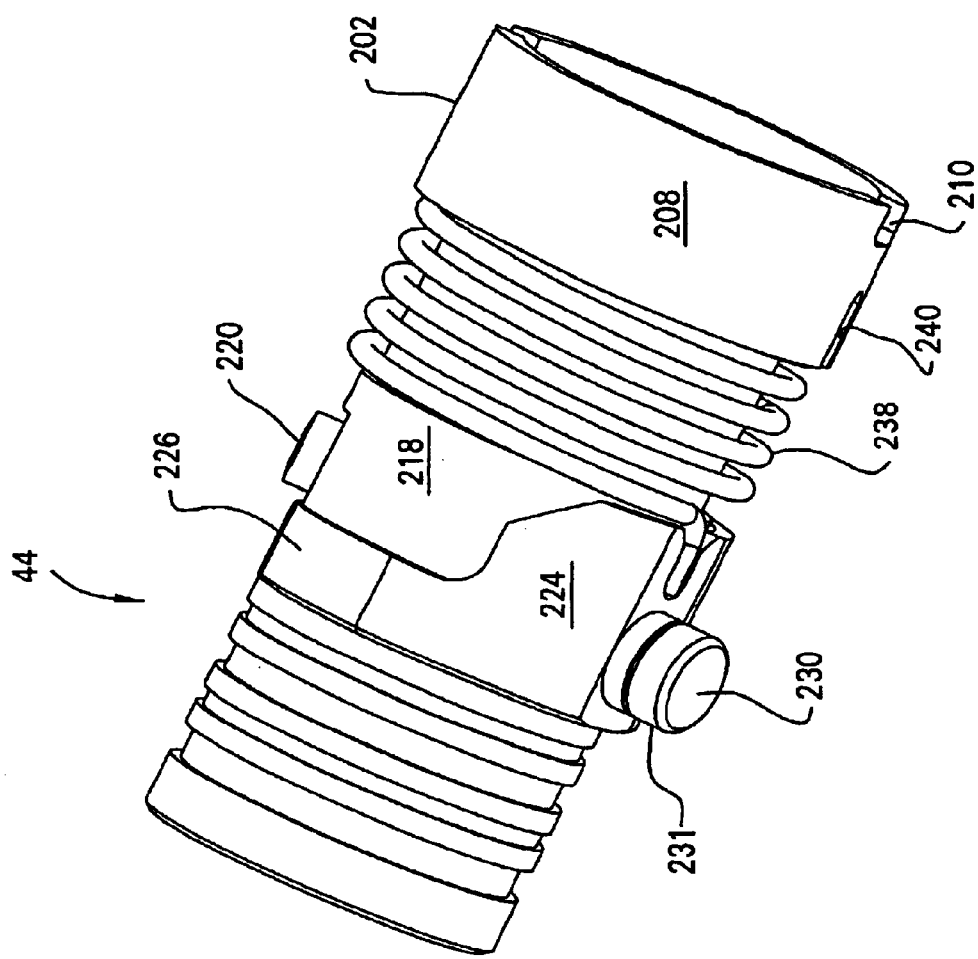
FIG. 7 is a perspective view of the lock assembly.

Lock assembly 44 is now described generally by reference to FIGS. 7, 8 and 9. The lock assembly 44 includes a multi-section, generally tubularly shaped housing 202 that is disposed in the body main bore 41. A bore 204 extends axially through housing 202. Housing 202 is further formed to have a proximally-located base 208 that has the largest diameter of the different sections of the housing. More particularly, housing base 208 is dimensioned to closely slip-fit against the inner wall of handpiece body 40 that defines bore 41. The proximal end of base 208 abuts the distal-facing face of the outer race of bearing assembly 190. Base 208 thus holds housing 202 off of retainer ring 192. In the Figures opposed slots 210 are seen in the proximal end of base 208. Slots 210 are designed to accommodate a tool used to insert, align and remove housing 202.

A dynamic seal 212 is located immediately inside the proximal end opening of bore 204 in the housing base 208. Dynamic seal 212 is similar in structure to previously described dynamic seal 170. Dynamic seal 212 extends between the inner wall of base 208 that defines bore 204 and the adjacent outer surface of low speed head nose 194. Seal 212 thus provides a liquid-tight barrier between the low speed head 142 and lock assembly housing 202. Housing 202 is further formed so that, internal to the base 208 there is an inwardly-directed, circumferentially extending lip 214 that extends into bore 204. Lip 214 thus prevents the forward movement of seal 212.

Forward of base 208, housing 202 has a waist 216 with a outer diameter less than that of base 208. Forward of waist 216 housing 202 has a shoulder 218 with a diameter between that of the base 208 and waist 216. An anti-rotation pin 220 extends through an opening in housing shoulder 218 into bore 204, (opening not identified). Forward of the location at which pin 220 is seated, the housing shoulder 218 is formed to have an arcuate slot 222 that extends partially around the housing.

Figure 10:
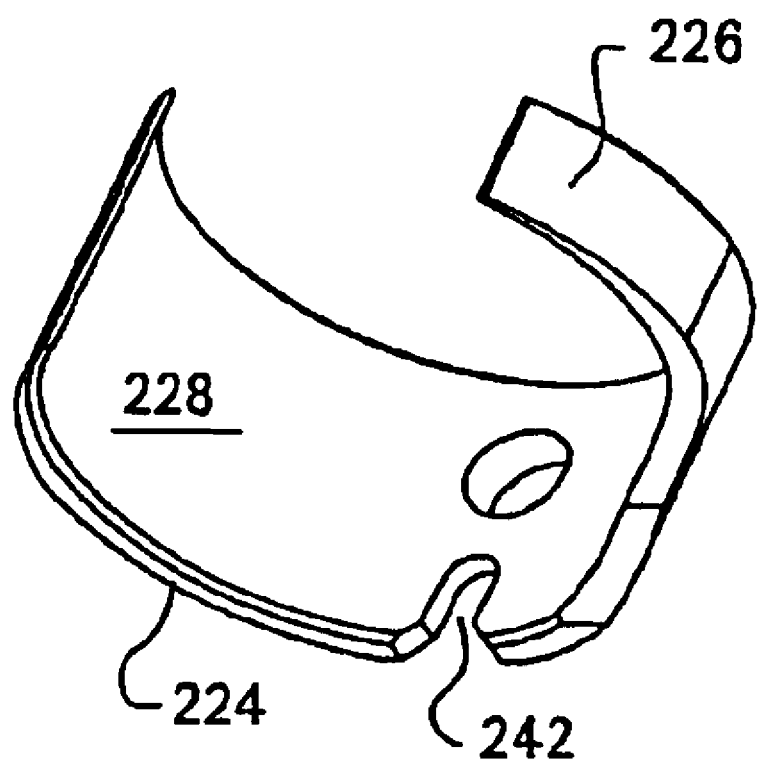
FIG. 10 is a perspective view of the release collar of the lock assembly.

An arcuately shaped release collar 224, best seen in FIG. 10, is fitted around housing shoulder 218. The release collar 224 is generally C-shaped and is further formed so that the collar can rotate around the underlying housing shoulder 218. Collar 224, it will be observed, is shaped so that one end, end 226, has a relatively short length as opposed to the opposed end, end 228. The release collar 224 is fitted to the housing 202 so that collar end 226 is located adjacent and forward of anti-rotation pin 220. Thus, when the release collar 224 is rotated, end 226 is able to clear pin 220.

A release pin 230 is seated in a hole 232 in release collar 224. The release collar is formed to define a rim, (not illustrated) that extends upwardly around hole 232. Pin 230 has a head 231 that is dimensioned to extend above collar 224 and through an arcuate slot 236 formed in the handpiece body 40, (FIG. 2B). Pin 230 also has a base section that extends through housing slot 222 into bore 204 and handpiece bore 41.

A helical torsion spring 238 biases the release collar and pin 224 and 230, respectively, in a locked position. The torsion spring 238 is disposed over the housing waist 216. One end of the spring 238 seats in a slot 240 formed in the outer surface of the housing base 208. The opposed end of spring 238 is seated in a slot 242 formed in the release collar 224. In the illustrated version of the invention, slot 242 is longitudinally aligned with collar hole 232. This need not always be the case. Collectively housing 202, release collar 224 and spring 238 are designed so that when these components are assembled, the release pin 230 abuts an edge of housing slot 222 and the spring places a biases the collar so that the release pin is pressed against the adjacent edge surface.

Extending forward from shoulder 218, housing 202 has a neck 240. Neck 240 is formed to have a number of circumferentially extending grooves 242. Distal to neck 240 housing 202 has a head 244 with an outwardly threaded surface. When the handpiece 22 of this invention is assembled, lock assembly housing 202 is held in bore 41 by a nut 246 (FIG. 2B) that is secured over head 244. Nut 246 is designed to be slip fit in a counterbore 248 that extends inwardly from the distal end of handpiece body 40. Nut 246 thus prevents rearward movement of the lock assembly 44.

When the lock assembly 44 is fitted in body 40, the distally-directed face of base 208 seats against an annular step that defines two different diameter sections of bore 41, (step not identified). This abutment of housing 202 against the inner wall of the body 40 blocks forward movement of the lock assembly 44.

When the handpiece is assembled, O-rings 250 are seated in grooves 242 of the lock assembly housing 202. The O-rings 250 thus function as a seal between the housing 202 and the adjacent inner wall of the handpiece body 40 that defines bore 41.

Returning to FIGS. 2A, 2B and 3, back cap 39 is now discussed. Back cap 39 includes a plate 256 that covers the open end of the body 40. The back cap 39 is further formed to have a head 258 that is in form of a block that extends rearwardly from plate 256 beyond the handpiece body 40. Plate and head 256 and 258, respectively, are collectively formed to define a first through hole, hole 260, that is aligned with the center axis of body bore 41. Fitting 43 extends through hole 260 on both sides of the back cap 39. A second hole, hole 262, extends through the plate 256 and head 258 below hole 260. The distal end of tube 110 is secured in hole 262.

Back cap 39 is further formed to have a third hole, hole 264, that extends through plate 256 and head 258. Hole 264 is located above hole 260 and is axially aligned with the fluid supply bore 46 formed in the handpiece body 40. Inlet fitting 50 extends rearwardly out of the proximal end opening of hole 264. When handpiece 22 is assembled, an elongated tube 266 is seated in the proximal end of the fluid supply bore 41 and extends a short distance beyond the portion of the body 40 that defines bore 46. The proximal end of tube 266 is located in back cap hole 264. Thus, hole 264 and tube 266 collectively define the fluid path between fitting 50 and fluid supply bore 46.

Back cap 39 is further formed to have stem 268 that extends forward from plate 256. Stem 268 is located between holes 260 and 264 and shares a common horizontal axis with hole 260. A bore 269 extends through stem 268. The back cap 39 is further formed so that a branch conduit, (not illustrated) provides a fluid communication path between the opening of hole 264 and bore 269.

Figure 3:
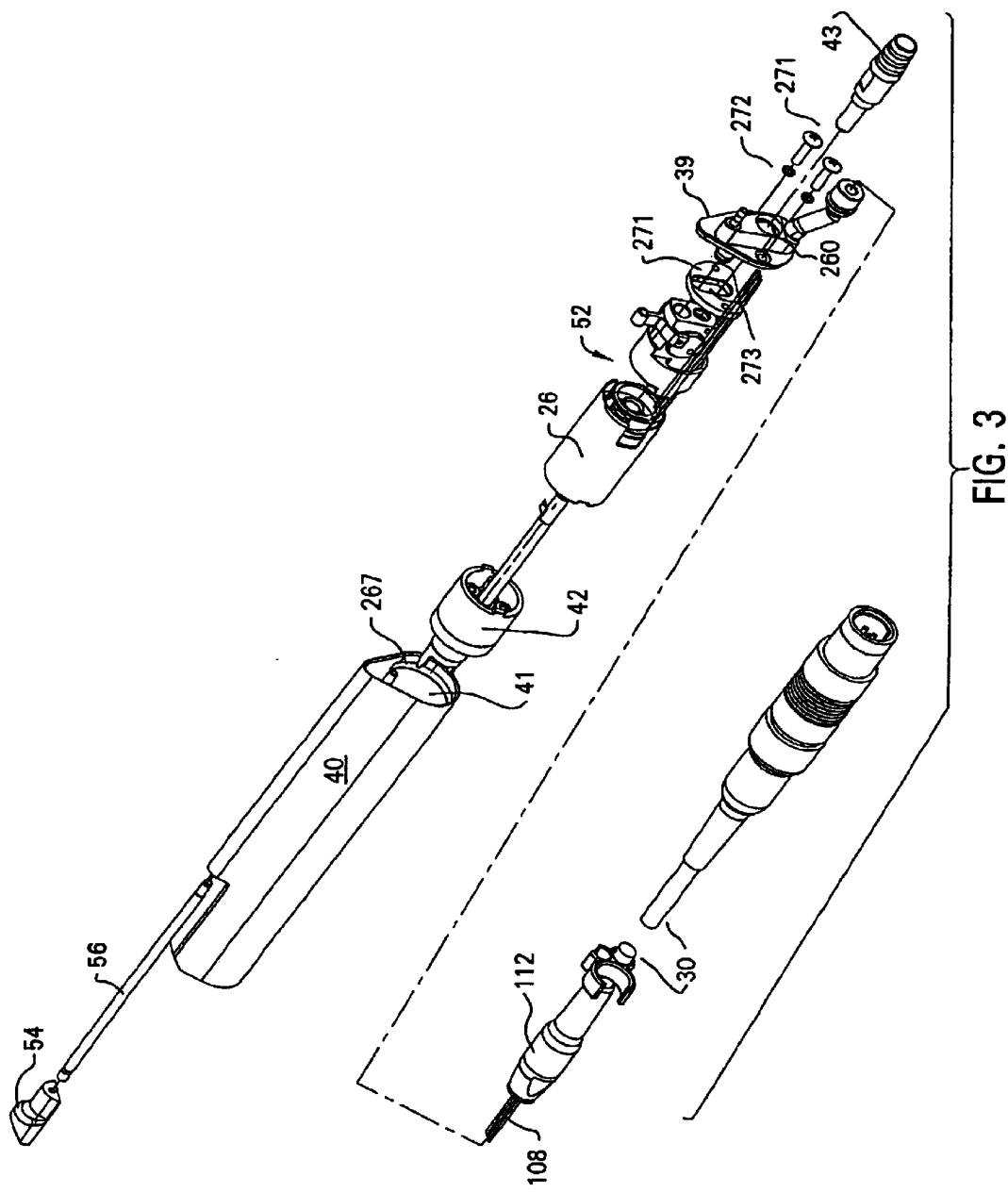
FIG. 3 is an exploded view of the handpiece of the surgical tool system of this invention.

A lock plate 270, seen best in FIG. 3, is secured in housing bore 41 immediately in front of back cap 39. In one particular version of the invention, it will be noted that the proximal end opening of bore 41 has a tear drop shape cross sectional profile. Lock plate 270 is cam fitted in an arcuate groove 267 formed in the inner wall of body 40 that defines the wide diameter portion of the open end of bore 40. Lock plate 270 serves as the static member against which back cap 39 is secured by fasteners 271. Washers 272 are located between the heads of the fasteners 271 and the back cap 39. The fasteners 271 in the lock plate 270 are secured into threaded openings in the lock plate 270, (openings not identified). Lock plate 270 is formed to have an oval-shaped center opening 273. The stem of fitting 43 and back cap stem 268 extend through opening 273. Lock plate 270 does not extend to the bottom of bore 41 so as to provide a space through which the flex circuit tail 106 can extend.

Figure 11:
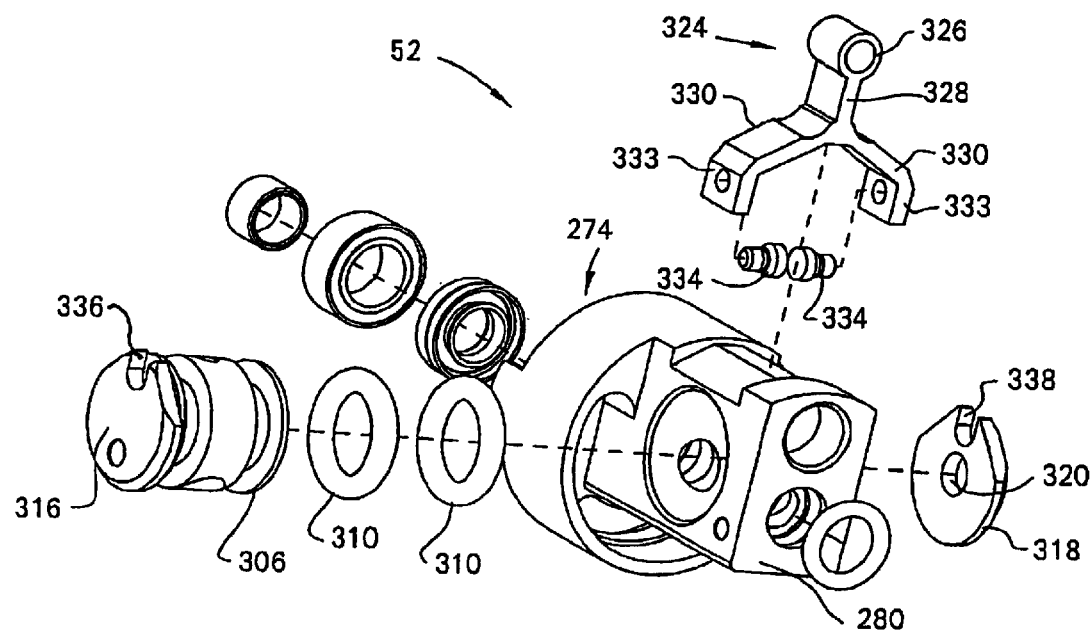
FIG. 11 is an exploded view of the valve.
Figure 12:
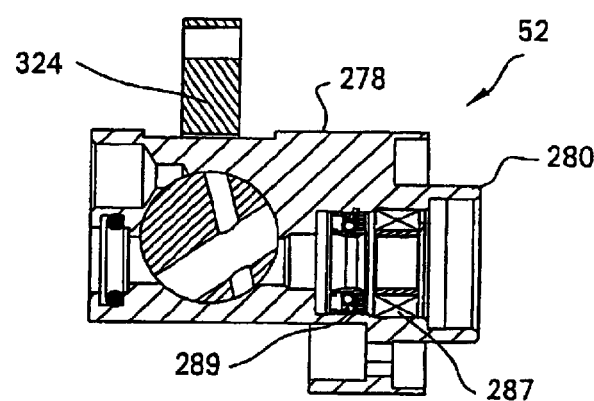
FIG. 12 is a cross-sectional of the valve.
Figure 13:
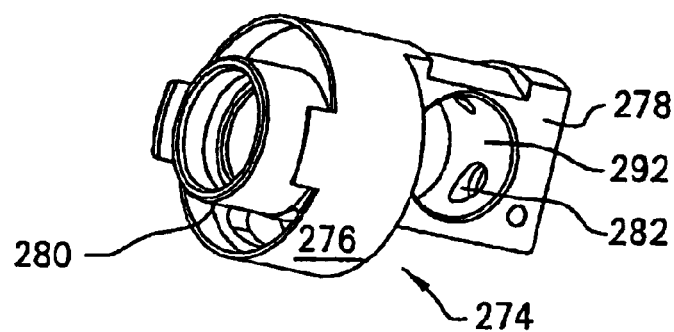
FIG. 13 is a perspective view of the valve housing.
Figure 14:
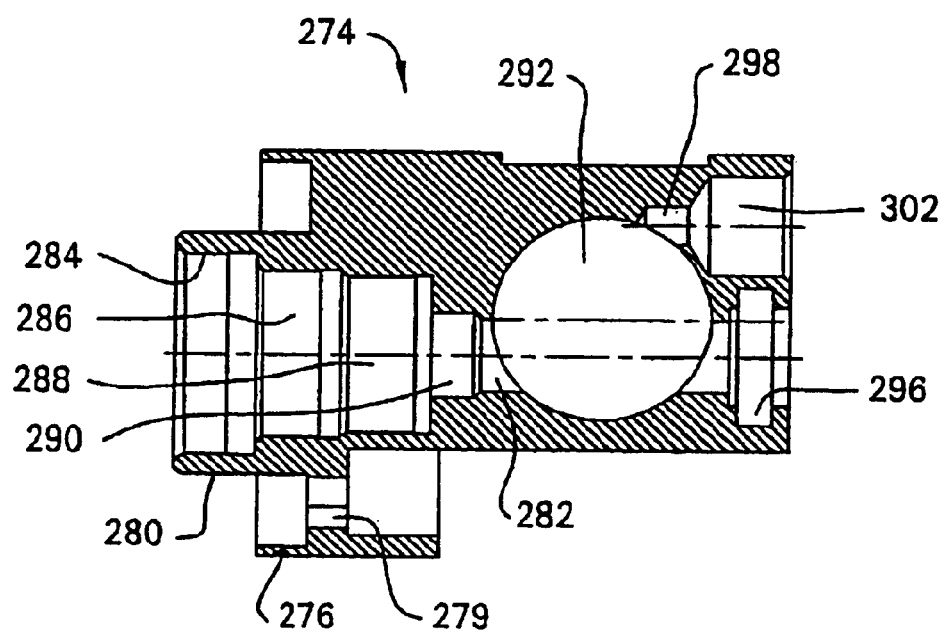
FIG. 14 is a cross-sectional view of the valve housing.

Valve 52, seen best in FIGS. 11 and 12, includes a valve housing 274. The housing 274, described primarily by reference to FIGS. 13 and 14, has a ring shaped collar 276. Collar 276 is dimensioned to closely fit in main bore 41. A block 278 is integrally formed with collar 276 and extends downwardly from the collar. Block 278 is shaped so as to have a circular head 280. When handpiece 22 is assembled, the outer circular wall of collar 276 seats against the inner circular wall of motor back shell base 98. Block 278 is further shaped so that there is an opening 279 in collar 276. Opening 279 functions as a through passage for conductors 106.

Block 278 is further formed to have a multi-section bore 282 that extends through the block and is coaxially aligned with head 280. More particularly the block is formed so that, extending proximally from the distal end of head 280, bore 282 has a first, second, third and fourth counterbores 284, 286, 288 and 290, respectively, of increasingly smaller diameters. When handpiece 22 is assembled, motor rotor shaft 66 seats in first counterbore 284. Motor tube 124 is disposed in the first, second and third counterbores 284, 286, and 288, respectively. As seen in FIG. 2A, a bearing assembly 285 extends between the proximal end of rotor shaft 66 and the wall of block 278 that defines the first counterbore 284. A bearing assembly 287 rotatably holds motor tube 124 in the second counterbore 286. A dynamic seal 289 is disposed between the proximal end of motor tube 124 and the surrounding circumferentially extending wall of block 278 that defines third counterbore 288.

Block 278 is further formed to define a circular valve bore 292 that intersects bore 282. More specifically, valve bore 292 has a longitudinal axis that extends perpendicular to the longitudinal axis of bore 282. The longitudinal axis of the valve bore 292 is located above the longitudinal axis of bore 282. Block 278 is formed so that valve bore 292 completely intersects bore 282.

When handpiece 22 is assembled, a stem section of fitting 43 that has a relatively narrow outer diameter, is seated in the portion of block bore 282 that is proximal to valve bore 292. An O-ring 294 seated in a groove 296 contiguous with bore 282 extends around the outer surface of the fitting stem section. O-ring 294 thus provides a seal between fitting 43 and the adjacent inner wall of block 278 that defines bore 282.

Block 278 is further formed to define a supplemental bore 298 that is located above and laterally axially aligned with bore 280. The supplemental bore 298 extends proximally from a portion of valve bore 292. The stem 268 of back cap 39 seats in a counterbore 302 formed in block 278 that extends from the supplemental bore 298. An O-ring 304 is seated in groove 305 formed in the distal end of stem 268 that is seated in counterbore 302. O-ring 304 thus provides a seal between the adjacent outer surface of stem 268 and the inner wall of block 278.

Figure 15:
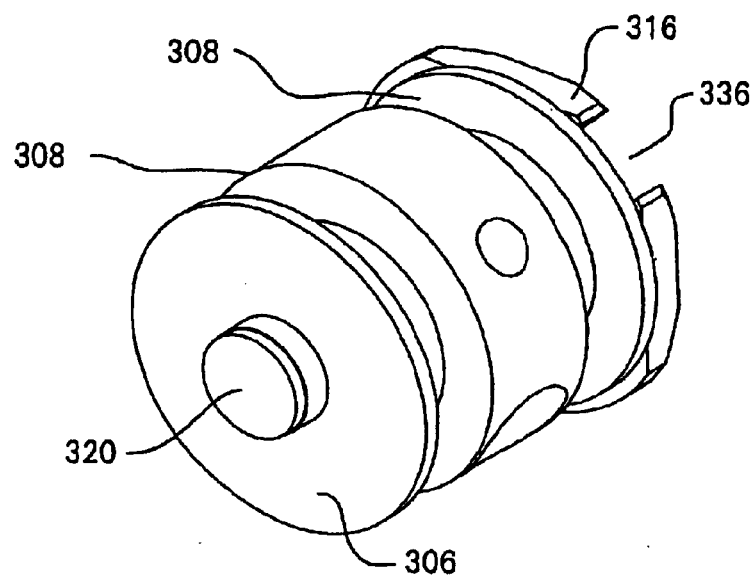
FIG. 15 is a perspective view of the valve member.
Figure 16:
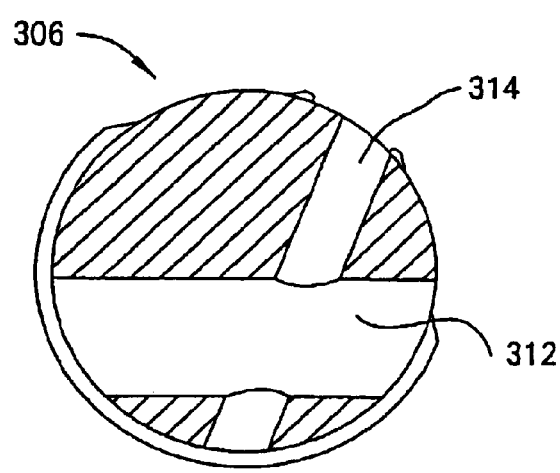
FIG. 16 is a cross-sectional view of the valve member.

Valve 52 includes a valve member 306 that is rotatably mounted in valve bore 292. The valve member 306, best seen by reference to FIGS. 15 and 16, has a generally disk-like shape. Valve member 306 is further formed to have two spaced apart, parallel grooves 308 that extend circumferentially around the outer curved surface of the member. An O-ring 310 is seated in each groove 308 so as to provide a seal between the adjacent outer surface of the valve member 306 and inner surface of block 278.

Valve member 306 is further formed to have two through bores 312 and 314 that intersect. A first one of the bores, bore 312, has the same diameter as block bore 282. Valve member 306 is formed so that when the member is in a first select rotational orientation within block 278, bores 282 and 312 are axially aligned. The second bore, bore 314 has a diameter less than that of bore 312. Bore 314 is located within valve member 306 so that when the valve member is in a second select rotational orientation, bore 314 establishes a fluid communications path between the distal portion of bore 282, the portion in front of valve bore 292, and the supplemental bore 298.

Valve member 306 is further formed to have a head 316 on one side of the member. Head 316 has an outer diameter greater than the diameter of valve bore 292. A disk-like lock plate 318, which has the same diameter as head 316, is fitted over the end of valve member 306 opposite head 316. Lock plate 318 is press fit over a boss 320 that extends outwardly from the adjacent surface of valve member 306. More specifically, boss 320 is press-fit into a hole 322 in the center of lock plate 318 owing to their size, head 316 and lock plate 318 collectively hold valve member 306 in the valve bore 292.

A valve guide 324 connects linkage rod 56 to valve member 306. The valve guide 324 has a ring shaped head 326 in which the proximal end of linkage rod 56 is secured. A neck 328 extends downwardly from head 326. Two opposed arms 330 extend outwardly away from neck 328. Each arm 330 is generally diagonally downwardly oriented and is further shaped to have an end flat palm section 333 that extends vertically downward. Valve guide pins 334 connect the opposed ends of valve member 306 to valve guide 324. More particularly, each guide pin 334 has a head and stem, (heads and stems not identified). The head of a first guide pin 334 is seated in a U-shaped slot 336 that is formed in valve member head 316. The head of the second guide pin 334 is seated in a similarly shaped slot 338 formed in lock plate 318. The pin stems each rotatably extend through an opening in the adjacent palm section 333 of valve guide 324, (openings not identified).

Figure 19A:
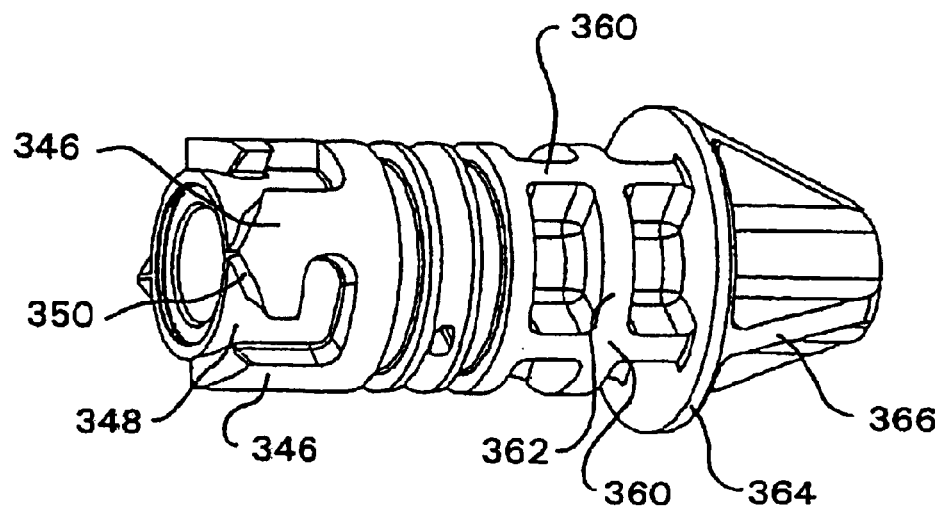
FIGS. 19A and 19B are, respectively, perspective and cross-sectional views of an outer hub of the cutting accessory.
Figure 19B:
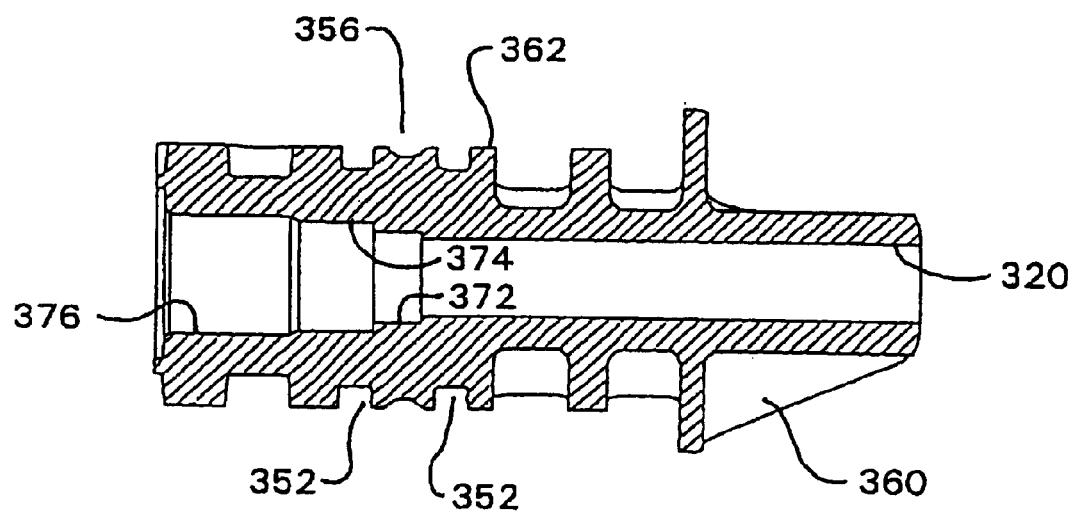

FIGS. 17 and 18 depict the basic components of one cutting accessory 24 that can be used with system 20 of this invention. Cutting accessory 24 includes a tubularly-shaped outer housing 340. The particular cutting accessory, a shaver, is constructed so that the distal end of outer housing 340 is closed. A small window 342 is formed in outer housing 340 proximal to the closed distal end tip of the housing. An outer hub 344, seen best in FIGS. 19A and 19B, is secured to the proximal end of the outer housing 340. Outer hub 344 is a generally tubular member that extends a short distance beyond the distal end of the proximal end of outer housing 340. The outer hub 344 is formed to have a set of spaced apart, generally L-shaped teeth 346. Teeth 346 are shaped to define lock slots 348 between the teeth. Teeth 346 are further shaped so that the proximal facing faces 350 are shaped to have a V-shaped profile, the apexes being the most proximal points of the teeth.

Extending distally from teeth 346, the outer hub 344 is shaped so as to have two spaced apart, circumferentially extending grooves 352 in the outer surface of the hub. Grooves 352 are shaped to accommodate O-rings 354. The outer hub 344 is further shaped so as to have a relatively shallow concave groove 356 in the outer surface between grooves 352. A bore 358 extends through the outer hub from the base of groove 356 to the underlying axially extending bore in the center of the hub.

Extending distally from the portion of the outer hub 344 that defines the most distal groove 352, the hub is formed to have a set of longitudinally extending spaced apart webs 360. An outwardly directed circumferentially extending flange 362 intersects webs 360. Webs 360 abut and terminate at the proximally directed face of a flat ring 364 also part of outer hub 344. Webs 366, which are aligned with webs 360, extend forward from the distally directed face of ring 364 to the distal end of the outer hub 344. Webs 366 have a triangular profile such that they are at their widest distance from the center axis of hub 344 at the points from which they extend forward from ring 364. Webs 360, flange 362, ring 364 and webs 366 provide structural strength to the outer hub 344. Providing webs 366 also simplifies the process of forming the outer hub 344.

Outer hub 344 is further formed so that the interior has a number of coaxially extending bores that are centered along the longitudinal axis of the hub. A housing bore 370 extends from the distal end of the hub 344 to a portion of the hub that is subtended by the section that defines the distal most groove 352. Housing bore 370 is the portion of the outer hub 344 in which the proximal end of housing 340 is seated. A reservoir bore 372 extends proximally from housing bore 370. Reservoir bore 372 has a diameter wider than that of housing bore 390. Reservoir bore 372 is subtended by the portion of the hub that defines groove 356. Laterally extending bore 358 opens into reservoir bore 372. A first counterbore 374 extends proximally from the proximal end of reservoir bore 372. First counterbore 374 has a diameter greater than that of reservoir bore 372. A second counterbore 376 extends distally from the reservoir bore 374 to the proximal end of the outer hub 344. Second counterbore 376 has a wider diameter than first counterbore bore 374. The outer hub 344 is formed so that the inner walls that define the bores have a short tapered section 378 that defines the transition between the counterbores 374 and 376.

A tubular rotating shaft 380 is disposed inside housing 340. The distal end of shaft 380 is closed. Extending proximally from the distal end, shaft 380 is formed to have a window 382. The window 382 is defined by edge surface 384 formed in the shaft 380. Window 342 of housing 340 is defined by a similarly sharp beveled edge 343 of the housing. Thus, edges 343 and 384 function as scissors when shaft 380 is rotated.

The Applicant's Assignee's U.S. Pat. No. 6,342,061, SURGICAL TOOL WITH INTEGRATED CHANNEL FOR IRRIGATION, issued Jan. 29, 2002, and incorporated herein by reference, provided additional discussion regarding how the distal end of a cutting accessory may be constructed. It should likewise be recognized that alternative cutting accessories, such as burs and resectors, can be constructed in accordance with this invention.

Figure 20A:
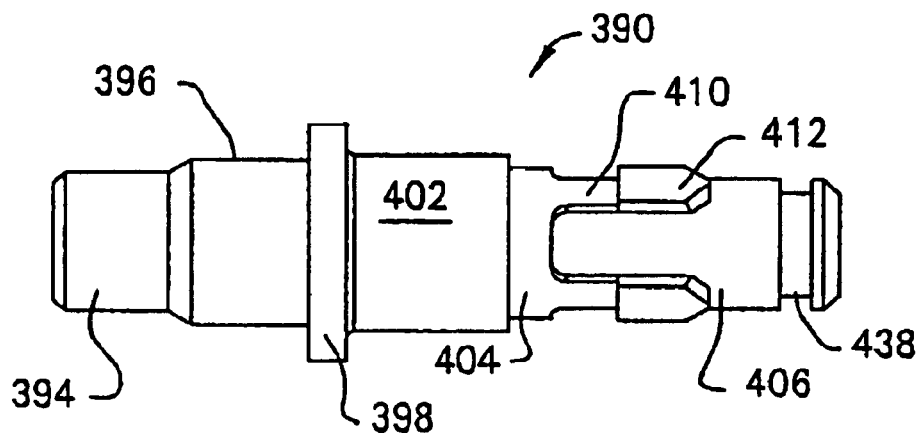
FIGS. 20A and 20B are, respectively, side and perspective views of a high speed drive hub of a cutting accessory.
Figure 20B:
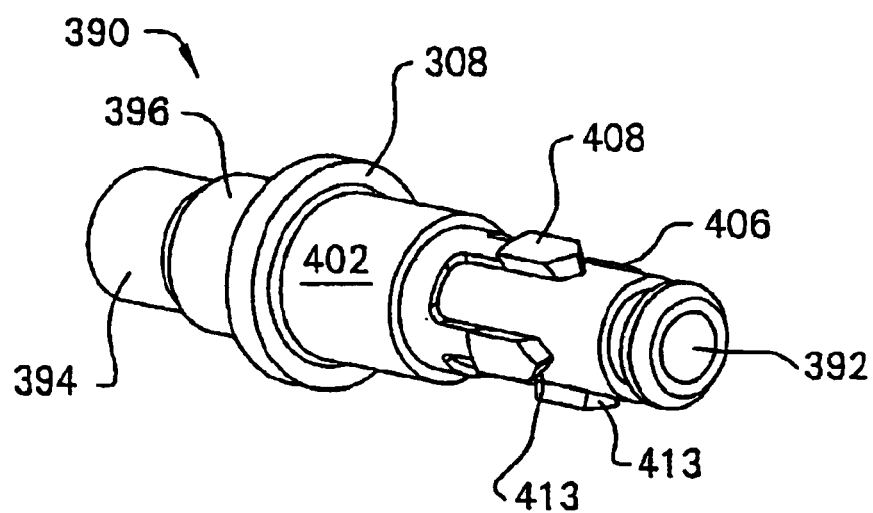

A drive hub is attached to the proximal end of rotating shaft 380. Some cutting accessories 24 of this invention are provided with a drive hub 390, now described by reference to FIGS. 20A and 20B, that is designed to engage teeth 138 of high speed head 128. Drive hub 390, hereinafter, the high speed drive hub, has a generally cylindrical body. A bore 392 extends axially through the hub 390. High speed drive hub 390 is formed to have a head 394 with a relatively narrow outer diameter and a proximally adjacent neck 396 that has a wider diameter. Not identified is a tapered section between head 394 and neck 396. A ring shaped collar 398 extends around the distal end of neck 396. Collar 398 has an outer diameter greater than that of neck 396. While not illustrated, internal to the high speed hub 390, the hub is formed with a counterbore within head 394, neck 396 and collar 398 that is coaxial to bore 392. This counterbore is the portion of the drive hub 390 in which the proximal end of rotating shaft 380 is heat staked or otherwise secured.

Extending proximally from collar 398, drive hub 390 is formed to have a cylindrically shaped torso section 402. Torso section 402 has a diameter slightly greater than that of neck 396. Proximal to torso section 402 the drive hub 390 has a skirt section 404 that has a diameter less than that of torso section 402. A cylindrical stem 406 extends proximal to skirt section 404. Stem 406 has a diameter less than that of skirt section 404.

High speed drive hub 390 is further formed to have four spaced apart parallel teeth 408 that extend proximally from skirt section 404 of stem 406. Each tooth 408 has a distal section 410 that extends directly from skirt section 404 that has the same radial outer diameter as the skirt section. Each tooth also has a proximal section 412 that is raised relative to the distal section 410. Proximal sections 412 of teeth 408 have proximal facing faces 413 that are pointed.

A spring 414 is disposed around high speed drive hub 390. The spring is located over skirt section 404 and teeth distal sections 410. When the cutting accessory 24 with which the high speed drive hub 390 is integral is fitted to handpiece 22, spring 414 thus extends between the distal end of the high speed drive head 128 and the circumferentially stepped surface between the hub torso and skirt sections 402 and 404, respectively. Spring 414 thus urges drive hub 390 and shaft 380 forward so that the distal end of the shaft abuts the adjacent inner surface of the distal end of housing 340.

Figure 21A:
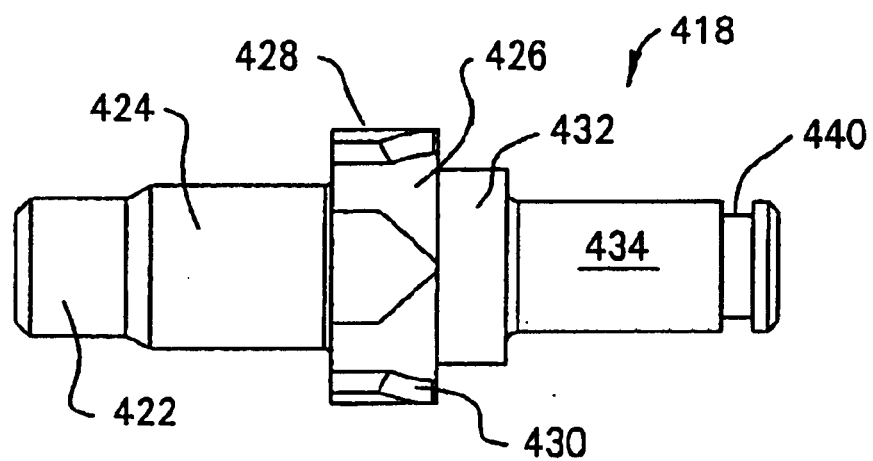
FIGS. 21A and 21B are, respectively, side and perspective views of a low speed drive hub of a cutting accessory.
Figure 21B:
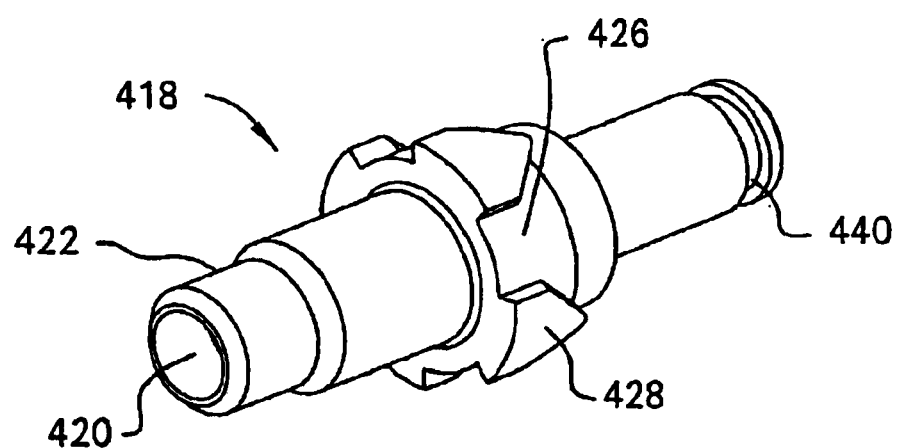

Alternatively, a low speed drive hub, hub 418 illustrated in FIGS. 21A and 21B may be secured to the proximal end of drive shaft 380. Hub 418 is incorporated into a cutting accessory 24 intended for connection to low speed head 142. Drive hub 418 has a bore 420, a head 422 and a neck 424, similar in shape to bore 392, head 394 and neck 396 of high speed drive hub 390. Neck 424 of the low speed drive hub 418 extends further along the length of the hub than neck 396 of the high speed drive hub 390. Internal to low speed drive hub 418 is a counterbore, (not illustrated), that extends through head 422 and neck 424 that is coaxial with bore 420. This counterbore is the space internal to the drive hub 418 in which the proximal end of shaft 380 is secured.

Located proximal to neck 424, drive hub 418 is formed to have a collar 426 that extends outwardly from the neck. A number of spaced apart teeth 428 are formed on the outer surface of collar 426. Teeth 428 have pointed, proximally directed faces 430. Extending rearwardly from collar 426 drive hub 418 has a cylindrical shoulder section 432 that has a diameter between that of neck 424 and collar 426. Proximal to shoulder section 432, the low speed drive hub 418 has a stem 434. Stem 434 is dimensioned to closely slide fit within the open end gear train high speed head 128.

Figure 23:
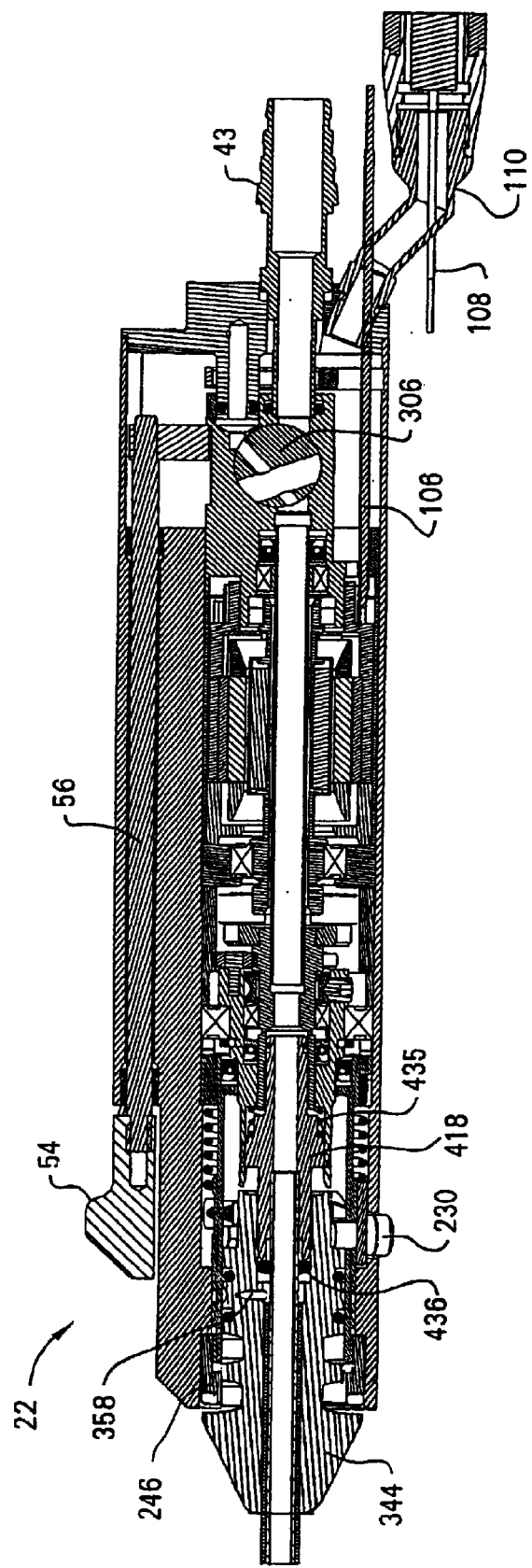
FIG. 23 depicts how a cutting accessory with a low speed drive hub is coupled to a handpiece.

A spring 435 (FIG. 23) extends over the shoulder and stem 432 and 434, respectively, of the low speed drive hub 418. When a cutting accessory 24 that includes the low speed drive hub 418 is coupled to handpiece 22, spring 435 extends between the circumferential step surface between low speed drive bore 144 and counterbore 196 and the circumferential step between hub collar 426 and shoulder 432. Spring 435 pushes drive hub 418 and rotating shaft 380 forward for the same reason spring 414 places a similar force of shaft 380.

When a cutting accessory 24 is assembled, an O-ring 436 (FIG. 18) is fitted to the hub stem. This O-ring 436 is fitted in a groove 438 formed in the proximal end of high speed drive hub stem 406 or a groove 440 formed in the same location of the low speed drive hub stem 434. The O-ring 436 functions as a seal between the drive hub stem 406 or 434 and the adjacent inner wall of the gear train high speed head 128. An O-ring 442 is located over the head 394 or 422 of drive hub 390 or 418. O-ring 442 thus provides a seal between the shaft 380 and the adjacent inner surface of outer hub 344.

While not illustrated and not part of the invention to which this application pertains, it should be understood that a memory chip may be fitted in the cutting accessory outer hub 344. The memory chip contains data that describes the operating characteristics of the cutting accessory 24. A coil is disposed in the distal end of handpiece body 40 so as to subtend the portion of the outer hub 344 in which the memory chip is seated. When the cutting accessory 24 is secured in the handpiece 22, data in the memory are inductively read by the control console 28 through cable 30 and the coil in the handpiece. The data read from the cutting accessory memory are used to regulate the actuation of motor 26. A more complete understanding of this feature is found in the Applicants' Assignee's U.S. patent application Ser. No. 10/214,973, SURGICAL TOOL SYSTEMS THAT PERFORM INDUCTIVE DATA TRANSFER, filed 8 Aug. 2002, now U.S. Pat. No. 6,769,906 and incorporated herein by reference.

The surgical tool system 20 of this invention is prepared for use by plugging the proximal end of power cable 30 to control console 28. Suction line 38 is attached to fitting 43; supply line 34 is connected to inlet fitting 50.

A cutting accessory 24 is then inserted in the distal open end of handpiece main bore 41. Both main bore 41 and the portion of the outer hub 344 inserted in the bore are cylindrical. The outer hub 344 has a number of lock slots 348 the entry to which is defined by the pointed faces 350 of teeth 346. Collectively, this means that medical personnel inserting the cutting accessory 24 in place do not have to concentrate on aligning the cutting accessory 24 in a select orientation relative to the handpiece 22 to ensure that the components will couple.

Instead, the abutment of one of the cutting accessory teeth 346 against release pin 230 causes the hub or release pin to be rotated so that the pin seats in the longitudinal portion of one of the slots 348. As the outer hub is further pressed into the handpiece 22, anti-rotation pin 220 seats in the longitudinally extending section of a second one of the slots. Once the release pin 230 is positioned in the laterally extending portion of the slot 348 in which the pin 230 is seated, spring 238 rotates the release collar 224 and pin 230 back to their static positions. This displacement of the release pin 230 seats the pin in the laterally extending portion of slot 348 that is spaced from the open ended longitudinally aligned portion. Thus, when the release pin 230 is in this position, the pin holds the cutting accessory 24 to the handpiece 22.

A cutting assembly 24 is removed from the handpiece 22 by the simple manual, arcuate displacement of release pin 230. This motion aligns the release pin with the longitudinally extending section of the outer hub slot 248 in which the pin is seated. Once the release pin 230 is so aligned, it is a simple task to simply pull the cutting accessory out of the bore 41 so a new accessory can be installed.

Figure 22:
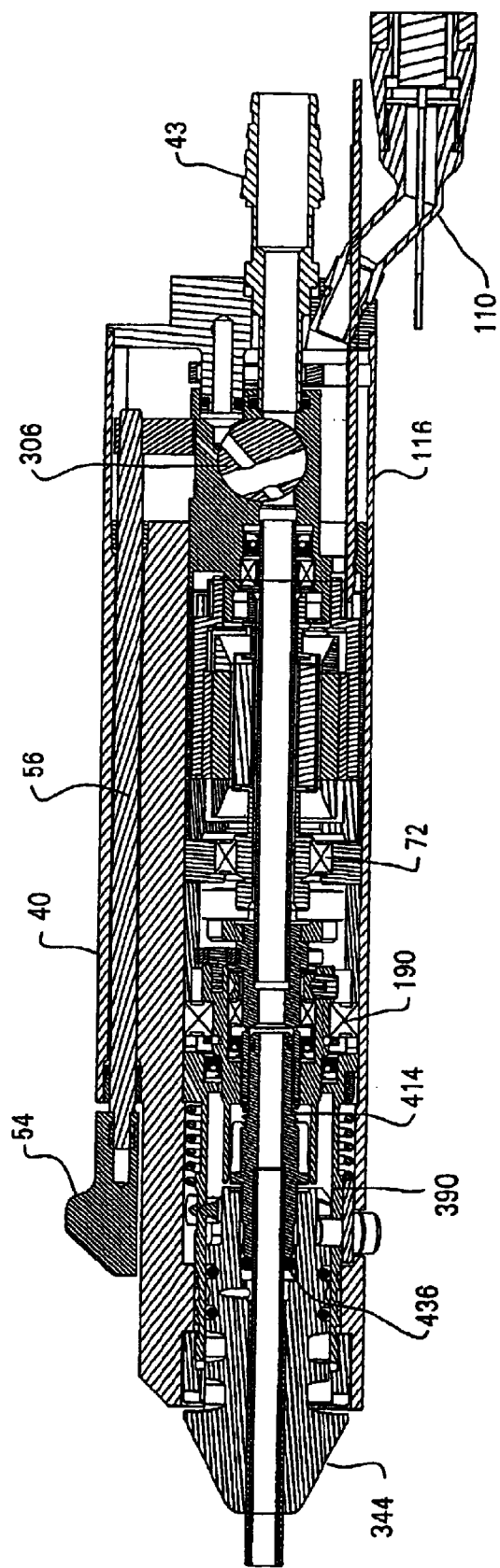
FIG. 22 depicts how a cutting accessory with a high speed drive hub is coupled to a handpiece.

The insertion of the cutting accessory 24 into the main bore 41 also results in the coupling of the drive hub 390 or 418 to the gear train head 128 or head 142, respectively. When the cutting accessory 22 is provided with high speed drive hub 390, high speed head teeth 138 seat between adjacent hub teeth proximal sections 412 as seen in FIG. 22. When the cutting accessory 24 is provided with the low speed drive hub, low speed head teeth 198 seat in the slots between adjacent hub teeth 428 shown in FIG. 23. Given the profiles of the opposed faces of teeth pairs 138/408 and 198/428 and, since thee drive hubs have more inter-teeth slots than there are complementary head teeth, the drive hub, upon insertion into the main bore automatically rotates to lock into the appropriate complementary head 128 or 148 of the gear train. Thus, again, medical personnel do not need to spend time aligning the drive hub when the cutting accessory 24 is fitted to the handpiece 22 to ensure that it is properly coupled to the gear train.

Another feature of the surgical tool system 20 of this invention is that, when the cutting accessory 24 is secured in the handpiece bore 41, outer hub groove 356 is aligned with the body with the open end of body discharge bore 48. Thus, irrigating fluid, when forced through the handpiece 22 by pump 32, is discharged from bore 48 into groove 356. O-rings 354 prevent longitudinal flow of the fluid through bore 41. Thus, the irrigating fluid is forced to flow through bore 358 in the outer hub 344. From bore 358 the fluid flows proximally in the annular space between housing 340 and shaft 380 and out window 342. Thus, the system of this invention is further designed to automatically establish a flow path for irrigation fluid from the handpiece 22 into the cutting accessory 24 without medical personnel having to either make an additional line connection or having to ensure that, when the cutting accessory is fitted to the handpiece, these two components are in a select orientation.

Still another advantage of the above feature of the surgical tool system 20 of this invention is that cutting accessory 24 can be placed in different rotational orientations relative to handpiece 22. In the particular version of the invention, the accessory can be selectively positioned in one of four rotational orientations that are spaced 90° apart from each other. This means the windows 342 and 348 of the cutting accessory, the cutting element, can be placed in one of four rotational orientations relative to the handpiece 22. Thus, a surgeon using the system of this invention can selectively position the cutting accessory so that it is most favorable position relative to the handpiece 22 to perform the desired surgical task.

The cutting accessory is actuated by the surgeon depressing a control member connected to the control console 28. Often this control member is a foot switch, (not illustrated). In alternative versions of the invention the control member may be a hand switch (not illustrated) the components of which are wholly or partially disposed within handpiece body 40.

The depression of the control member results in the control console supplying a current to energize motor 26. In some versions of the invention, the motor 26 operates at speeds between 4,000 and 60,000 RPM. This is the speed at which rotor shaft 66 turns. The toothed surface of the gear train housing 116, gears 132 and carrier 130 form a first planetary gear assembly. In some versions of the invention, this assembly steps down the speed of the output rotation of motor tube 124 relative to rotor shaft 66 at ratio of from 2.8:1 to 5.0:1.0. When the cutting accessory 24 is provided with a high speed drive hub 390, the hub engages motor tube 124 through teeth 138 so as to rotate in unison with the motor tube.

Toothed ring 137, gears 182 and the toothed inner surface of gear train housing 116 form a second planetary gear assembly. This assembly steps down the rotational moment of the low speed head 142 relative to that of the high speed head 128 at a ratio of from 2.8:1 to 5.0:1. When cutting accessory 24 is provided with a low speed drive hub 418, the hub engages the low speed head 142 to rotate in unison with this head.

Thus, depending which drive hub 390 or 418 is connected to a cutting accessory, an accessory may be driven at a speed that is between 20 or 36% of the output speed of the rotor shaft 66 or 4 to 13% of the output speed of the rotor shaft speed. An advantage of this feature of the system of this invention is that cutting accessories can be operated at a relatively wide range of speeds relative to the motor speed.

Valve 52 regulates fluid flow through the bore that extends axially through drive shaft 380. It is anticipated that often the valve 52 will be set so that valve member bore 312 is wholly or partially aligned with block bore 282. When the valve member 306 is so positioned there is, respectively, a full or partial suction is drawn by pump 36 through the drive shaft. It should be understood that the valve member bore 312 is wholly aligned with block bore 282 when handpiece button 54 is in its most distal position, shown best in FIG. 2A. The retraction of button 54 proximally results in a like displacement of rod 56 and valve guide 324. The rearward displacement of valve guide 324 results in the rotation of valve member 306 that turns the bore out of alignment with bore 282. When valve member bore 312 is aligned to any degree with block bore 282, the second valve member bore 314 is wholly out of alignment with supplemental bore 298.

The further rotation of valve member 306 brings it into the position illustrated by FIG. 22. Here, bore 312 is out of registration with bore 282 and bore 314 establishes a fluid communications path between bore 282 and supplemental bore 298. Thus, when the valve 52 is in this state, irrigating fluid is supplied through bores 298, 314 and 282 and the drive hub bore to the center of the cutting accessory shaft 380. This fluid, since it is under pressure, flushes debris from the shaft. The fluid may also be used to, when desired, apply additional irrigating fluid to the surgical site to which the cutting accessory is applied.

The above description is limited to one specific version of the invention. Other versions of the invention may vary from what has been described. Thus, there is no requirement that all versions of the system of this invention include all of the described features. For example, some versions of the invention may only include the gear train assembly but not the assembly for automatically supplying irrigating fluid to the outer hub of the cutting accessory. Alternatively, other versions of the invention may only include the assembly for supplying irrigating fluid to the outer hub and not the gear train assembly.

It should also be recognized that other versions of the invention may have other features than those that have been described. For example, there is no requirement that all versions of the invention include an electrically driven motor let alone a brushless, sensorless, electric motor. In other versions of the invention alternative power generating units may be integral with the system handpiece. Alternative power generating units that may be incorporated into this invention include: pneumatically driven motors; light emitting devices, including lasers; electrosurgical members; and sound or ultrasonic generators. When a system of this invention with an alternative power generating unit is provided, again, it may not be necessary to provide all the features of the system disclosed in this application.

Alternative versions of this invention may have features that are different from what has been described. For example, alternative constructions of a gear train capable of receiving different drive hubs and driving those hubs at different speeds may be provided. For example, in some versions of the invention, the motor rotor may run at a speed range which is appropriate to also actuate a cutting accessory. In these versions of the invention, a high speed head, capable of receiving an accessory high speed driver, may be attached to the motor rotor to turn in unison with the rotor. In these versions of the invention, only a single speed reduction gear assembly is provided; the low speed head being part of this gear assembly. Also, in other versions of the invention, the gear train may have three or more heads for driving the associated cutting accessory within three or more distinct speed ranges. These versions of the gear train would typically have at least two speed reduction gear assemblies.

Also, there is no requirement that the gear trains of alternative versions of the invention be only provided with speed reduction gear assemblies. For some versions of the invention, it may be desirable to provide the gear train with at least one gear assembly with an output head that turns at a rate faster than that of the associated input gear.

Similarly, it should be recognized that it may be possible to provide a gear train with plural drive heads each of which are capable of receiving a common cutting accessory drive hub. In these versions of the invention, a release or guide mechanism that is manually actuated may be provided to ensure that the drive hub is mated to the intended drive head.

It should likewise be understood that not all versions of the invention may have gears that form planetary gear assemblies. Alternative gear assemblies may be provided. For example, one such alternative assembly may include spur gears. In these versions of the invention, including versions of the invention provided only with gear assemblies, there is no requirement that the low speed drive head always be located forward of the high speed drive head. In alternative versions of the invention this arrangement of the drive heads may be reduced.

In the described version of the invention, the gears all rotate in the direction in which the motor shaft 66 rotates. This may not always be the case. In some versions of the invention it may be desirable to provide one or more gears that rotate in a direction opposite the direction of rotation of the motor shaft. An advantage of this version of the invention is that, when the motor is driven an oscillatory mode, shaft 66 is rotated in forward/reverse/forward/reverse pattern, the gears that rotate in the direction opposite of that of shaft 66 will offset the oscillatory kick that occurs when the other gears of the handpiece change rotational direction.

It should likewise be recognized that there is no requirement that in all versions of the invention with motors and gear trains, that the motors have cannulated rotors through which a suction from the handpiece is drawn. Clearly, this type of motor is not required if the system is not designed so that the system can be employed to draw a suction from the surgical site. Also, in alternative versions of the invention, the suction may be drawn through a bore in the handpiece body that is in addition to a substitute for the irrigating fluid supply bore. In these versions of the invention, the motor is a wholly sealed device, the only exposed member of which is the distal end of the output shaft. The gear train is seated in a chamber in the handpiece and the suction bore extends from the chamber.

It should likewise be recognized that alternative lock assemblies employed to releasably hold the cutting accessory to the handpiece. For exampled, in some alternative versions of the invention, the lock assembly may have one or more members that are designed to abut against and retract away from complementary seating spaces in the cutting accessory.

There may also be variations in the valve assembly incorporated into alternative versions of this invention. Clearly, in versions of the invention not provided with a fluid supply assembly, the valve would only control the suction drawn at the surgical site. If the motor does not have a cannulated flow conduit, the valve may be positioned in a location other than the proximal end of the handpiece. Also, some versions of the invention may not be provided with a fluid supply assembly configured to deliver fluid to the cutting accessory outer hub. These versions of the invention may still be provided with both a fluid inlet and suction outlet. Here, as in the described version of the invention, the valve may be designed to connect one conduit integral with the cutting accessory to either the fluid inlet or suction outlet.

In still other versions of the invention, the valve assembly may have a three state valve. That is a valve that, prior to switching the cutting accessory fluid connection from the suction fitting to the inlet fitting, completely closes the fluid connection to/from the cutting accessory.

Also, it should be understood that, in the current version of the invention, control console 28 is configured to actuate irrigation pump 32 simultaneously with the actuation of the handpiece motor 26 by the surgeon. The system is further configured to allow the surgeon to also turn pump 32 on and off independently of the actuation of motor 26. This control is typically through a foot switch attached to the control console 28. It is contemplated that, when irrigation flow through the center of cutting accessory shaft 380 is required, the surgeon will first stop motor 26. Thus, when the valve is first moved to establish an inlet fitting-to-accessory shaft fluid connection, irrigating fluid is not being forced into the handpiece. Thus, when the valve is in this state, there is no fluid flow to/from the cutting accessory shaft 380. In order to force irrigating fluid through the cutting accessory shaft 380 the surgeon is required to actuate the pump. Again, this is performed by depression of a foot switch or a button presented on the control console 26.

In an alternative version of the invention, the valve is assembled so that there is arc through which the valve member 306 can be rotated in which it will establish an inlet fitting-to-accessory shaft fluid communications path. A sensor is used to monitor the position of valve member 306. This sensor may take the form of a proximity sensor mounted in body 40 that generates a bistate signal as a function of the relative position of linkage rod 56. In these versions of the invention, the output signal generated by the sensor undergoes a state change when the valve in its further rotational position. The output signal generated by this sensor is applied to the control console and used to regulate the actuation of pump 32. Thus, initially when the valve member 306 is moved to establish the inlet fitting-to-accessory shaft fluid communications path, the signal produced by the sensor does not change. As button 54 is pushed further rearwardly the resultant displacement of the linkage rod 56 is detected by the sensor. As a result of the state change of the output signal from the sensor, control console 28 actuates pump 32 so as to force irrigating fluid through the cutting accessory shaft 380.

An advantage of the above version of the invention is that the surgeon, with a single member, button 54, is able to both set the valve and actuate pump 32. Thus, with the single button 54 the surgeon is able to place handpiece 22 into one of three state: a first state in which there is an accessory shaft-to-suction fitting connection; a second state in which there is an inlet fitting-to-accessory shaft connection without fluid flow, a no fluid flow state; and a third state in which there is fluid flowing from the pump 32 to the accessory shaft.

This configuration of the invention thus makes it possible to provide a three state fluid control with a single finger even though the valve member itself may be relative small, both diameter and length both 0.5 inches in size or smaller. It is necessary to provide valves of this size because the handpieces themselves are relatively small in size, typically having a maximum length of 6 inches and a maximum width of 1 inch or less. Moreover, it should also be understood that, within the handpiece, often up to 1 inch of its initial length may be the bore space in which the outer hub of the cutting accessory is seated. These bores are so long because in a handpiece designed for use with an image guided surgery system, it is necessary to fit the cutting accessory to the handpiece so that the position of the distal end of the accessory to the handpiece does not vary. It has been found that one ready way to ensure this type of securement is to design the system so that the outer hub tightly fits in the handpiece bore in which the hub is seated and that the hub have a relatively long length, for example. between 0.6 and 1.0 inches.

Thus, given that surgeons prefer working with handpieces that are relatively small in size and that the space in the front ends of handpieces are designed to accommodate a large sized hub, there is little space in the handpiece to accommodate a valve. Even in view of these design factors, the valve assembly of this invention allows a surgeon to, with a single on valve control member, set the valve so that a suction is drawn through the cutting accessory shaft 380, the shaft is closed to fluid inflow/outflow or irrigating fluid is forced down the shaft.

It should be similarly recognized that alternative constructions of the valve may be provided. In some versions of the invention, the valve body may be disposed in the handpiece body so as to rotate around an axis that is coaxial and/or at least parallel with the longitudinal axis of the handpiece body. Alternatively, the valve may have a valve member that slidably moves in order to be placed into different valve states.

Also, while the components of one particular version of this invention are designed to perform sinus and throat surgery, it is understood that other versions of the invention are dimensioned to perform other surgical procedures, including, but not limited to, orthopedic surgery, general surgery and gynecological surgery. Also, while many versions of this invention are well suited to perform endoscopic surgical procedures, it should be understood that the use of this invention and its alternative designs are not so limited.

It should likewise be understood that, in some versions of the invention, the drive heads integral with the gear train may not be concentrically aligned.

Also, the geometry of the outer hub and drive hubs of the cutting accessory are exemplary, not limiting. For example, the number of axially aligned bore sections in the outer hub may be different from what has been described. There may even just be a single, constant diameter bore. Similarly, it may be desirable to provide plural lateral irrigation inlet bores into the axial bores. Also, for the outer hub, only single type of surface member is shown for receiving the complementary handpiece locking member. Similarly, for each of the drive hubs, only a single type of surface member is shown for facilitating the coupling of the hub to the complementary drive head. Clearly, the shape and size of these surface members may be different in other cutting accessories of this invention when these accessories are designed for use with handpieces that having alternative lock assemblies and/or drive heads.

Also, while in some preferred versions of the invention, it is possible to position the cutting accessory in different rotational positions relative to the handpiece, in other versions of the invention, this feature may not be necessary or desired. In these versions of the invention, the cutting accessory may only be provided with a single surface feature or member designed to facilitate its attachment to the handpiece in a specific angular orientation.

Similarly, the outer hub may be provided with an alternative arrangement of surface members or features that allow the hub, and therefore the cutting accessory, to be mounted to the complementary handpiece in more or less than four positions as described in the exemplary embodiment. In some versions of the invention, collectively the handpiece lock assembly and the surface features of the outer hub may be designed to allow the mounting of the hub, and therefore the cutting accessory, to the handpiece in any angular orientation.

Thus, it is the object of the appended claims to cover all such variations and modifications that come within the true spirit and scope of the invention.

What is claimed is:

1. A surgical handpiece for actuating a cutting accessory, said handpiece having:
   a body;
   a motor disposed in said body, said motor having a rotating output shaft;
   a first drive head rotatably disposed in said body and connected to said motor output shaft to rotate upon the rotation of said output shaft;
   a second drive head rotatably disposed in said body, said second drive head having a coupling member designed to receive a cutting accessory drive hub so that the drive hub rotates in unison with the second drive head;
   said first drive head having a coupling member designed to receive a cutting accessory drive hub so that the drive hub rotates in unison with said first drive head while
   a first gear assembly connects said second drive head to said motor output shaft and said first gear assembly drives said second drive head upon actuation of said motor output shaft and drives said second drive head at a rotational speed different than the rotational speed at which said first drive head is rotated.

2. The surgical handpiece of claim 1, further including a second gear assembly extending between said motor output shaft and said first drive head and said second gear assembly being configured to drive said first drive head upon action of said motor output shaft and at a rotational speed different than the rotational speed at which said motor output shaft turns.

3. The surgical handpiece of claim 2, wherein: said second gear assembly drives said first drive head at a speed less than the rotational speed at which said motor output shaft turns; and said first gear assembly drives said second drive head at a speed less than the rotational speed at which said first drive head turns.

4. The surgical handpiece of claim 1, wherein: said first drive head is shaped to receive a first cutting accessory drive hub; and said second drive head is shaped to receive a second cutting accessory drive hub that is different in shape or dimension from the first cutting accessory drive hub.

5. The surgical handpiece of claim 4, wherein:
   said first drive head is shaped to define a bore for receiving the first cutting accessory drive hub, the bore having a diameter; and
   said second drive head is shaped to define a bore for receiving the second cutting accessory drive hub, the bore having a diameter, the diameter of the bore of said second drive head being greater than the diameter of the bore of the first drive head.

6. The surgical handpiece of claim 1, wherein said motor output shaft is a tubular member that has a through bore; said first drive head has a through bore; and said second drive head has a through bore, said through bores being coaxially aligned with each other.

7. The surgical handpiece of claim 6, further including a motor tube connected to and extending from one of said drive heads, said motor tube extending through said motor output shaft.

8. A surgical handpiece for actuating a cutting accessory, the cutting accessory having a drive hub, said handpiece including:
   a body, said body having a bore;
   a motor disposed in said body, said motor having a rotating output shaft;
   a first drive head rotatably secured in the body bore, said first drive head having at least one member for engaging a cutting accessory drive hub so as to rotate the drive hub;
   a first gear assembly connected between said motor output shaft and said first drive head, said first gear assembly having at least one gear sized to transfer rotational power of said output shaft to said first drive head and to rotate said first drive head at a rotational speed less than the rotational speed of said output shaft;
   a second drive head rotatably secured in the body bore, said second drive head having at least one member for engaging a cutting accessory drive hub so as to rotate the drive hub; and
   a second gear assembly connected between said motor output shaft and said second drive head, said second gear assembly having at least one gear for transferring rotational power of said first drive head to said second drive head, said at least one gear being dimensioned to drive said second drive head at a rotational speed less than the rotational speed at which said first drive head is rotated.

9. The surgical handpiece of claim 8, wherein at least one of said first or second gear assemblies is a planetary gear assembly.

10. The surgical handpiece of claim 8, wherein:
    said motor output shaft is a tubular shaft; and
    said first drive head and said second drive head are each formed with a bore, the drive head bores being coaxial with said motor output shaft.

11. The surgical handpiece of claim 10, further including a motor tube extending from said drive head closest to said motor, said motor tube extending into said tubular shaft forming said motor output shaft.

12. The surgical handpiece of claim 1, wherein:
    the bore of said body has an open end in which the cutting accessory is seated; and
    said first and second drive heads are rotatably mounted in the body bore so that said first drive head is located between said motor and said second drive head.

* * * * *

UNITED STATES PATENT AND TRADEMARK OFFICE
CERTIFICATE OF CORRECTION

PATENT NO.        : 6,958,071 B2
APPLICATION NO.   : 10/251646
DATED             : October 25, 2005
INVENTOR(S)       : Steven Carusillo et al.

Page 1 of 1

It is certified that error appears in the above-identified patent and that said Letters Patent is hereby corrected as shown below:

On the title page, please change
Item "[75] Inventors:    Steven Carusillo, Kalamazoo, MI (US);
                         Bruce D. Henniges, Kalamazoo, MI
                         (US); Milton Barnes, Fort Worth, TX (US)"

to Item -- [75]  Inventors:   Steven Carusillo, Kalamazoo, MI (US):
                              Milton Barnes, Fort Worth, TX (US) --.

Signed and Sealed this

Eleventh Day of December, 2007

JON W. DUDAS
*Director of the United States Patent and Trademark Office*